(12) United States Patent
Layton et al.

(10) Patent No.: US 11,497,801 B2
(45) Date of Patent: Nov. 15, 2022

(54) COMPOSITIONS AND METHODS OF ENHANCING IMMUNE RESPONSES

(71) Applicants: Sherryll Layton, Lisbon, NH (US); Jeffrey W. Hall, Minneapolis, MN (US)

(72) Inventors: Sherryll Layton, Lisbon, NH (US); Jeffrey W. Hall, Minneapolis, MN (US)

( * ) Notice: Subject to any disclaimer, the term of this patent is extended or adjusted under 35 U.S.C. 154(b) by 0 days.

(21) Appl. No.: 17/180,012

(22) Filed: Feb. 19, 2021

(65) Prior Publication Data
US 2022/0265802 A1 Aug. 25, 2022

(51) Int. Cl.
| | | |
|---|---|---|
| *C12Q 1/68* | (2018.01) | |
| *A61K 39/015* | (2006.01) | |
| *A61K 39/012* | (2006.01) | |
| *A61K 39/39* | (2006.01) | |
| *A61P 33/02* | (2006.01) | |
| *A61K 39/002* | (2006.01) | |
| *A61K 39/00* | (2006.01) | |

(52) U.S. Cl.
CPC .......... *A61K 39/015* (2013.01); *A61K 39/002* (2013.01); *A61K 39/012* (2013.01); *A61K 39/39* (2013.01); *A61P 33/02* (2018.01); *A61K 2039/523* (2013.01)

(58) Field of Classification Search
None
See application file for complete search history.

(56) References Cited

U.S. PATENT DOCUMENTS 10,463,711 B2 * 11/2019 Hamill .................. A61K 38/10
2010/0196380 A1 * 8/2010 Lobo ...................... C12Q 1/025
424/139.1

FOREIGN PATENT DOCUMENTS

WO WO2015048342 A2 * 4/2015

* cited by examiner

*Primary Examiner* — Jennifer E Graser
(74) *Attorney, Agent, or Firm* — Blake E. Vande Garde; Avek IP, LLC

(57) ABSTRACT

A vaccine vector comprising a first polynucleotide encoding the antigenic polypeptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or any combination thereof.

12 Claims, 5 Drawing Sheets
Specification includes a Sequence Listing.

Figure 1: Taxonomic analysis using NCBI BLASTP suite showing apicomplexan homologs of the indicated amino acid sequences.

Figure 2. Daily and mean fecal scores of diary calves. (Figure 2A) The daily cumulative fecal scores for each treatment group, Vaccine and Control, (Figure 2B) mean and SD fecal score for study days 1-15, (Figure 2C) mean and SD fecal score for study days 16-20.

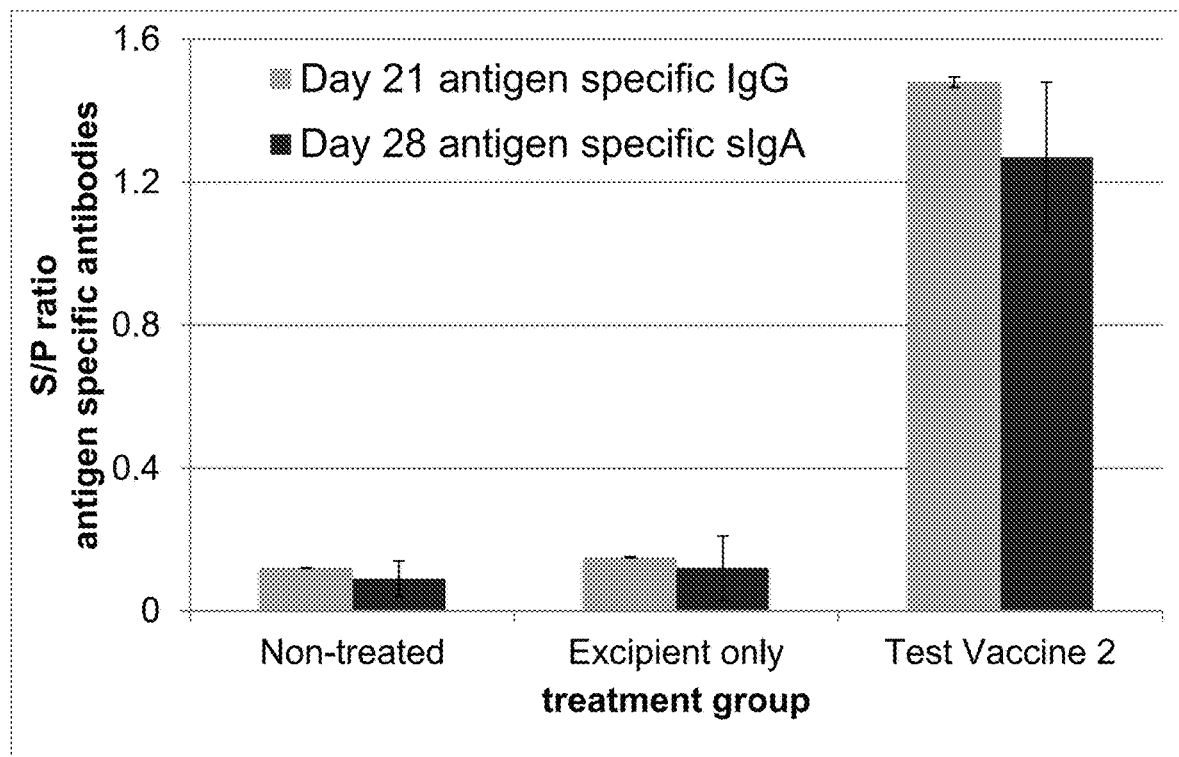

Figure 3. Test Vaccine 2 induces systemic and mucosal antibody responses.
ELISA quantification of serum IgG (21d of age, grey bars) and mucosal sIgA (28d of age, black bars) levels of non-treated control, excipient only, and Test Vaccine 2 treated chickens. The data are presented as mean S/P ratios (sample mean − negative control mean)/(positive control mean − negative control mean) ± SEM (n=10).

Figure 4A

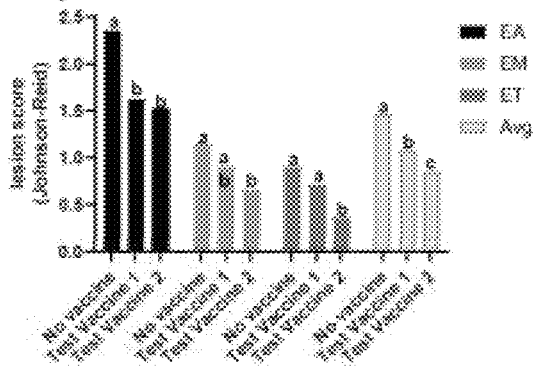

Figure 4B

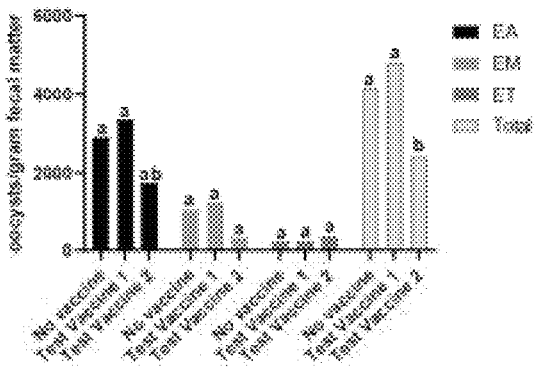

Figure 4C

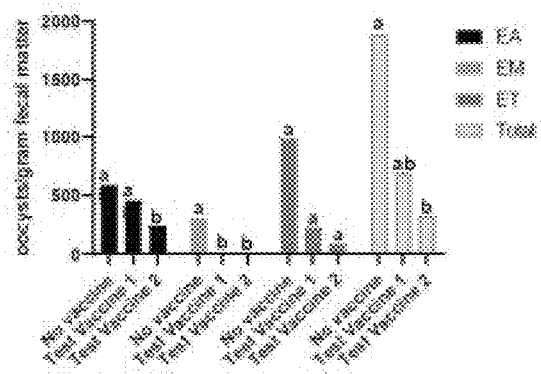

Figure 4D

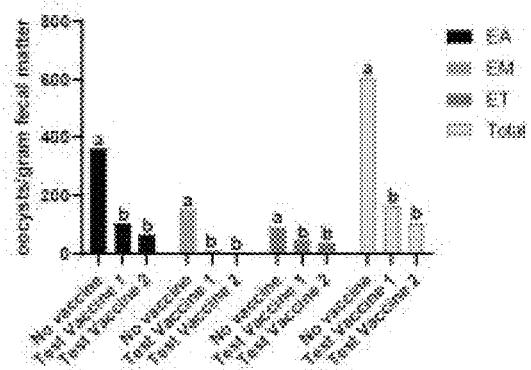

Figure 4. The inactivated subunit coccidia vaccine induces multi-species protection. (Figure 4A) Coccidial lesion scores on study day 27 in the gastrointestinal tract for *E. acervulina* (EA), *E. maxima* (EM), and *E. tenella* (ET) and total average lesion scores (Avg.) of five male broilers per pen per treatment group in clinical trial #1. Study day (Figure 4B) 28, (Figure 4C) 35, (Figure 4D) 42 coccidial shedding counts (oocysts per gram of fresh fecal material) for *Eimeria acervulina* (EA), *Eimeria maxima* (EM), *Eimeria tenella* (ET) and total average oocysts counts (Total) from clinical trial #1. Different letters indicated statistical significance between treatments ($p<0.05$).

Figure 5A

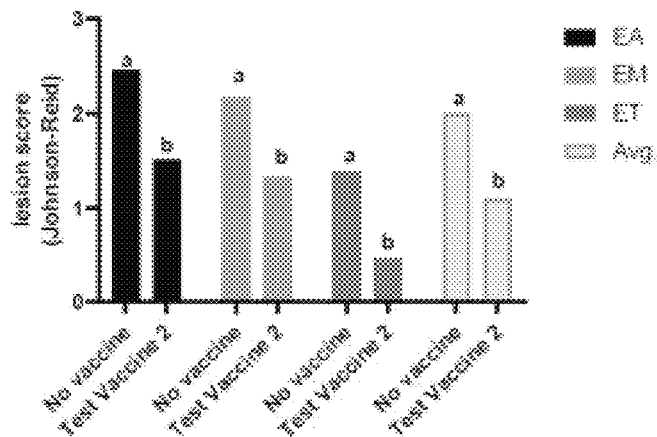

Figure 5B

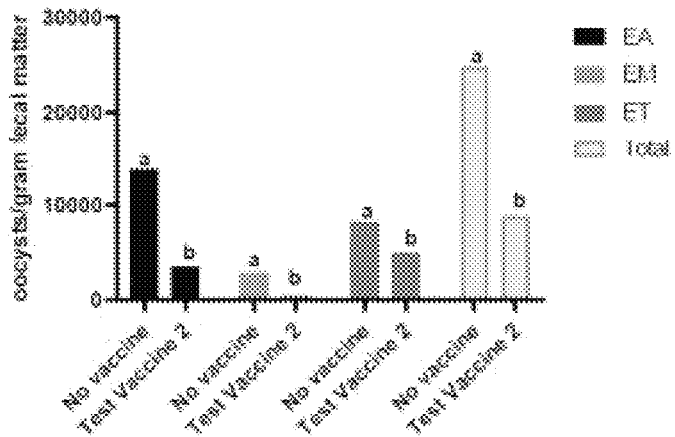

Figure 5. Test Vaccine 2 induces significant protection against coccidiosis.
(Figure 5A) Coccidial lesion scores on study day 27 in the gastrointestinal tract for *E. acervulina* (EA), *E. maxima* (EM), and *E. tenella* (ET) and total average lesion scores (Avg.) of five male broilers per pen per treatment group in clinical trial #2. Study day (Figure 5B) 28 coccidial shedding counts (oocysts per gram of fresh fecal material) for *Eimeria acervulina* (EA), *Eimeria maxima* (EM), *Eimeria tenella* (ET) and total average oocysts counts (Total) from clinical trial #2. Different letters indicated statistical significance between treatments ($p<0.05$).

COMPOSITIONS AND METHODS OF ENHANCING IMMUNE RESPONSES

FIELD OF INVENTION

The present invention is related to the fields of parasitology and vaccinology and more specifically to mucosal immunity in relation to parasitology and vaccinology.

BACKGROUND OF THE INVENTION

Coccidiosis in poultry is a common disease which has global importance in the commercial industry. Coccidiosis is caused by parasites of the genus *Eimeria*, belonging to Phylum Apicomplexa and continues to be one of the most economically important diseases in today's poultry industry facilitating a need to develop safe and effective vaccines which do not compromise productivity. The apicomplexan phylum of protozoa, characterized by the presence of an apical complex, contains numerous parasites of veterinary (*Cryptosporidium, Neospora, Eimeria*) and medical (*Plasmodium, Cryptosporidium, Toxoplasma*) importance. *Eimeria* ssp. are the causative agent of coccidiosis, which continues to be one of the most important enteric diseases in the commercial poultry industry, with losses to the industry estimated to be $800 million worldwide and $450 million in the United States annually. Coccidiosis manifests in the gastrointestinal tract (GIT), resulting in severe diarrhea and affecting growth performance with subsequent increases in feed conversion ratio and mortality in poultry. The life cycle of *Eimeria* is complex and involves both intracellular and extracellular stages. Each *Eimeria* spp., colonizes specific areas of the GIT depending on its tissue tropism.

Coccidiosis is primarily a disease that affects young animals but can affect older animals that are immune compromised. It occurs commonly in confined conditions but can occur in free-ranging conditions that have congregating areas, such as feeding, shade and watering areas. Coccidiosis causes substantial economic losses due to reduced performance, death from direct infections, and by predisposing poultry to secondary bacterial and viral infections, such as *salmonellosis*, or respiratory diseases. The labor demand for the treatment and care of infected poultry in addition to medication costs amplify the economic losses.

Conventional approaches of disease control have employed prophylactic medications in the form of chemotherapy, antibiotics, anticoccidials and selection of disease resistant strains of chickens. However, with the ability of parasites to develop drug resistance, research into alternative methods of disease prevention and control continue. In this regard, vaccination against coccidiosis has become a key aspect of present research. Current commercial vaccines are hindered by their complex production processes and species-specific protection.

Immunity to the disease is complex and involves many facets of the host immune system. There is definite interplay between humoral and cell-mediated immunity, even though it is accepted that cell-mediated immunity is most important. The parasite is known to colonize the intestinal epithelium and hence, the primary line of host defense is mucosal associated lymphoid tissue (MALT). The mucous membranes constitute the major portal of entry for infectious agents and include membranes of the respiratory, gastrointestinal, and genitourinary tract as well as the ocular conjunctiva, the inner ear, and the ducts of all exocrine glands. Collectively they cover more than 400 m² in humans and serve as the first line of defense against infection at the entry points for a variety of pathogens. The gastrointestinal system is the largest lymphoid organ in the body containing an estimated 70% to 80% of the body's immunoglobulin-producing cells. 80% of all the activated B cells in the body are located at the mucosal tissues.

The concept of a common mucosal immune system predicts that induction of immunity at one mucosal surface, such as the gut, can provide immunity at another mucosal surface, such as the lung providing a necessary link for immunity transfer throughout mucosal surfaces. Increasing evidence has indicated that mucosal vaccination can induce both systemic and local mucosal immunity, while systemic immunization generally fails to elicit strong mucosal immunity. Vaccines which are administered through a mucosal route of entry and are able to elicit mucosal, humoral, and cell-mediated immune responses offer a promising alternative approach when compared with existing traditional (inactivated subcutaneous or attenuated total pathogen oral) vaccine strategies.

The life cycle of *Eimeria* spp., is complex and involves both intracellular and extracellular stages. The parasite is known to colonize the intestinal epithelium and hence, the primary line of host defense is the MALT. Immunity to the disease is complex and involves many facets of the host immune system. There is definite interplay between humoral and cell-mediated immunity, even though it is accepted that cell-mediated immunity is most important. Species of *Eimeria* are potently immunogenic and are capable of eliciting a strong immune response.

Thus, there is clearly a need for both a product and method which alleviates parasitic affliction and coccidiosis.

SUMMARY OF THE INVENTION

The instant invention includes a vaccine for the protection of poultry against coccidiosis comprising an amino acid sequence as shown in SEQ ID Nos.: 1 through 9. Vaccines according to the present invention may be comprised within a vector, such as a virus, bacterium, or liposome.

The instant invention includes methods of enhancing the immune response against coccidiosis in a subject by administering a vaccine according to the present invention.

The instant invention also includes methods of reducing morbidity associated with infection with coccidiosis in a subject by administering a vaccine according to the present invention.

The instant invention includes vaccine for the protection of poultry against one or more Apicomplexan parasites comprising an amino acid sequence as shown in SEQ ID Nos.: 1 through 9 and a pharmaceutically acceptable carrier. Vaccines according to the present invention may be comprised within a vector, such as a virus, bacterium, or liposome.

The instant invention includes methods of enhancing the immune response against one or more Apicomplexan parasites in a subject by administering a vaccine according to the present invention.

The instant invention also includes methods of reducing morbidity associated with infection with one or more Apicomplexan parasites in a subject by administering a vaccine according to the present invention.

DESCRIPTION OF THE DRAWINGS

FIG. 1 is a Table of a taxonomic analysis using NCBI BLASTP suite showing apicomplexan homologs of the indicated amino acid sequences.

FIG. 3 is a bar graph showing the S/P ratios of Antigen Specific Antibodies, illustrating the induction of systemic and mucosal antibody responses.

FIG. 4A is a bar graph showing the lesion scores at study day 27 in the gastrointestinal tract for *E. acervuline* (EA), *E. maxima* (EM), and *E. tenella* (ET).

FIG. 4B is a bar graph showing the quantification of oocysts per gram of fecal matter at study day 28 for *E. acervuline* (EA), *E. maxima* (EM), and *E. tenella* (ET) and total average oocysts counts per gram of fecal matter.

FIG. 4C is a bar graph showing the levels of oocysts per gram of fecal matter at study day 35 for *E. acervuline* (EA), *E. maxima* (EM), and *E. tenella* (ET) and total average oocysts counts per gram of fecal matter.

FIG. 4D is a bar graph showing the levels of oocysts per gram of fecal matter at study day 42 for *E. acervuline* (EA), *E. maxima* (EM), and *E. tenella* (ET) and total average oocysts counts per gram of fecal matter.

FIG. 5A is a bar graph showing the lesion scores at study day 27 in the gastrointestinal tract for *E. acervuline* (EA), *E. maxima* (EM), and *E. tenella* (ET).

FIG. 5B is a bar graph showing the levels of oocysts per gram of fecal matter at study day 28 for *E. acervuline* (EA), *E. maxima* (EM), and *E. tenella* (ET) and total average oocysts counts per gram of fecal matter.

DETAILED DESCRIPTION

Figure 2A:
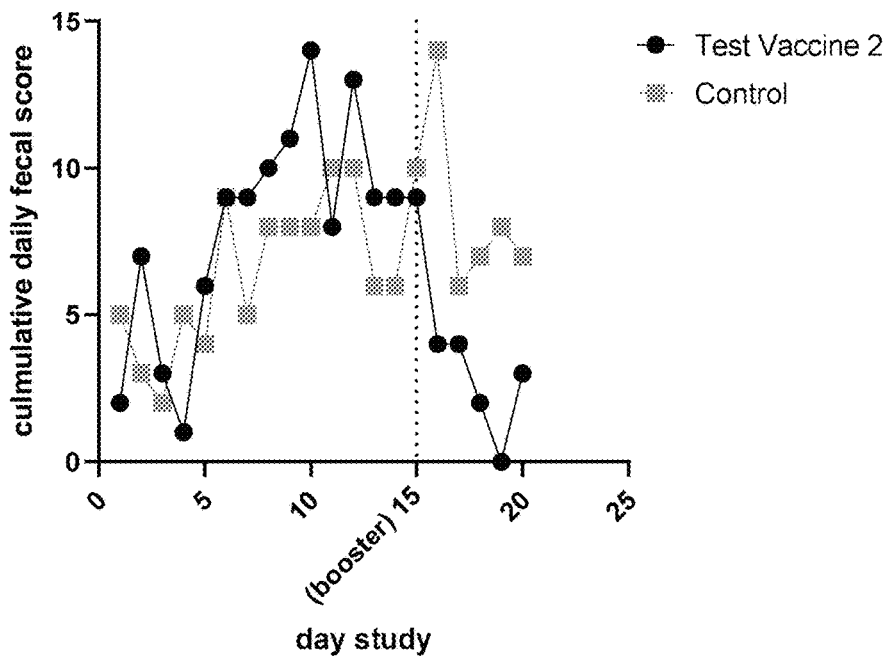
FIG. 2A is a graph showing the daily cumulative fecal scores for each treatment group, Vaccine and Control.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The apicomplexan phylum of protozoa contains numerous parasites of veterinary (*Cryptosporidium, Neospora, Eimeria, Cystoisospora* (formally known as *Isospora*)) and medical (*Plasmodium, Cryptosporidium, Toxoplasma*) importance. Apicomplexan parasites share a common substrate dependent locomotion termed gliding motility used for active host cell penetration and tissue migration. Secretion of apical organelles called micronemes and rhoptries leads to the formation of an intimate binding interface junction connecting host cell receptors and parasite adhesive proteins. Host cell invasion relies on the translocation of transmembrane adhesive proteins that form a bridge between the host cell and the parasite actomyosin motor which provides motive force for active penetration. When selecting the protective protein or subunit for inclusion in our universal inactive subunit vaccine against apicomplexan family there are several criteria which should be considered and met.

Vaccination against coccidiosis is one of the most sought out aspects of modern-day poultry research and is considered as a viable option for disease control. Ideally, the vaccine candidate should be able to stimulate a significant immune response, one that is capable of offering long-term protection. New and improved vaccine delivery methods are constantly being tested for their efficacy. In this regard, the field of vaccinology has recently undergone a transformation from a more traditional belief that systemic immunity is the only effective way to generate protection against infectious diseases to a more progressive thought process of effective immunity can be achieved through mucosal immunity. As stated previously, the mucous membranes constitute the major portal of entry for infectious agents and include membranes of the respiratory, gastrointestinal, and genitourinary tract as well as the ocular conjunctiva, the inner ear, and the ducts of all exocrine glands. Collectively they cover more than 400 $m^2$ in humans and serve as the first line of defense against infection at the entry points for a variety of pathogens. In fact, the only way to contract an infection other than the mucosal portal of entry is through blood-borne routes such as injections, transfusions and bites or other damage to epithelial surfaces (e.g., Staphylococcal infections causing impetigo from acne).

Despite its important role, only a handful of vaccines specifically target this area of the immune system despite strong evidence that a robust mucosal response can effectively prevent systemic infections. Most vaccine research to date have been centered around stimulating systemic immunity to create antibodies which will neutralize disease causing organisms once they have colonized, reproduced and crossed into the body's systemic environment. Increasing evidence has indicated that mucosal vaccination can induce both systemic and local mucosal immunity, while systemic immunization generally fails to elicit strong mucosal immunity. In the present study, a recombinant *Bacillus* sp. strain (Vaccine vector 1 (VV1)) was constructed that produces a heterologous protective protein or subunit from the Apicomplexan phylum of protozoa. To produce the final oral inactive subunit vaccine candidate, VV1 is cultured and formulated with a natural polysaccharide excipient to produce Test Vaccine (TV). TV was tested against a direct *Eimeria maxima* challenge, for its ability to stimulate mucosal immunity against selected epitopes and protect against disease. The use of a protective protein or subunit of the pathogen produced by an inert vector instead of the whole pathogen has been successfully tested for a variety of pathogens. When administered through a mucosal route of entry they are able to elicit mucosal, humoral, and cell-mediated immune responses offering a promising alternative approach when compared with existing traditional (inactivated subcutaneous or attenuated total pathogen oral) vaccine strategies.

The use of recombinant vectored vaccines for disease control and protection is well documented. Simple approaches to design and construction have been evaluated and used successfully in experimental models and a large number of parasite antigens have been employed as vaccine candidates to confer protection. Several vaccine vectors have emerged to date, all of which have relative advantages and limitations depending on the proposed application. However, bacterial vectors have been regarded as the front runner in vectored vaccine strategies. *Bacillus subtilis* provides a promising platform to produce vectored vaccines. Several *Bacillus* spp. are considered generally recognized as safe (GRAS) organisms with a very comprehensive record of safe oral consumption. Researchers have shown oral live *Bacillus* vaccine vectors expressing recombinant foreign antigens to stimulate systemic, mucosal, humoral, and cell-mediated immune responses against heterologous antigens. Furthermore, *Bacillus* has intrinsic probiotic properties, which increase the health of the host stimulating the innate immune response through the toll-like receptor pathways, fortify the gastrointestinal system by enhancing the production of tight junction repair proteins and down regulate the inflammatory response cause by pathogenic Gram-negative bacteria.

The few points offer beneficial evidence in favor of using *Bacillus* as a vaccine vector platform. The major benefit of using bacterial vectors is they offer mucosal routes of immunization, providing the possibility of greatly enhanced protection when compared to parenteral vaccination.

When selecting the protective protein or subunit for inclusion in our universal inactive subunit vaccine against apicomplexan family there are several criteria which should be considered and met:
1) the protein sequence should be highly conserved. More specifically the protein sequence should be identical for all the serotypes or strains of the species;
2) the protein must be accessible to the immune system on the pathogen;
3) the protein should be antigenic and immunogenic when presented alone in a recognizable fashion to the host;
4) the immune response (humoral or cell mediated but preferably both) should be relatively quick, efficient, protective, and long lasting.

The instant invention includes evaluating the immune response and cross-protection against three *Eimeria* spp. using a novel orally administered inactivated subunit coccidia vaccine against direct coccidial challenge.

Recombinant DNA technologies enable manipulation of many bacterial and viral species. Some bacteria and viruses are mildly or non-pathogenic while still capable of generating a robust immune response. These bacteria and viruses make desirable vaccine vectors for eliciting an immune response to a heterologous or foreign antigen. Bacterial or viral vaccine vectors may mimic the natural infection and produce strong and long-lasting immunity. Vaccine vectors are generally inexpensive to produce and administer. Additionally, such vectors can often carry multiple antigens and therefore provide protection against multiple infectious agents.

In one aspect, this invention relates to the use of *Bacillus* vectors in vaccination and generation of immune responses against protozoa and other pathogenic agents. *Bacillus* strains make suitable vaccine vectors because of the ability to make bacteria capable of expressing heterologous polypeptides. In addition, bacterial genes may be mutated or attenuated to create bacteria with low to no pathogenesis to the infected or immunized subject, while maintaining immunogenicity.

The ability of the *Bacillus* spp. to survive the gastrointestinal tract of the host and give rise to a mucosal immune response is documented. Oral vaccines using a *Bacillus* spp. vector produce a strong mucosal immune response and are generally easy to administer to both animals and humans. Lacking virulence capabilities and is a generally recognized as safe (GRAS) organism, *Bacillus subtilis*, is non-pathogenic and an exceptional manufacturing platform vector for producing industrial metabolites, chemicals, and heterologous recombinant proteins. Thus, *Bacillus subtilis* faithfully manufactures recombinant antigens that generate a strong protective immune response in many host subjects. A *Bacillus* strain that could be used for effective mucosal, e.g., oral, vaccination would provide a vector that could be used to readily and repeatedly vaccinate a subject against one or more pathogenic agents, such as coccidiosis.

Polynucleotides encoding polypeptide antigens from any number of pathogenic organisms may be inserted into the vaccine vector and expressed to generate antigenic polypeptides. An antigenic polypeptide is a polypeptide that is capable of being specifically recognized by the adaptive immune system. An antigenic polypeptide includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions.

The antigenic polypeptides may be full-length proteins or portions thereof. It is well established that immune system recognition of many proteins is based on a relatively small number of amino acids, often referred to as the epitope. Epitopes may be only 8-10 amino acids. Thus, the antigenic polypeptides described herein may be full-length proteins, 8 amino acid long epitopes or any portion between these extremes. In fact, the antigenic polypeptide may include more than one epitope from a single pathogen or protein. Suitably the antigenic polypeptide is a polypeptide that is not natively associated with the vector. Not natively associated includes antigenic polypeptides that may also occur natively in the vector, but that are being expressed recombinantly as an epitope, are being expressed in combination with a different polypeptide as a fusion protein to allow for differential display and differential enhancement of the immune response as compared to the natively expressed polypeptide.

Multiple copies of the same epitope or multiple epitopes from different proteins may be included in the vaccine vector. It is envisioned that several epitopes or antigens from the same or different pathogens or diseases may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time.

The polynucleotides may be inserted into the chromosome of the vaccine vector or encoded on plasmids or other extrachromosomal DNA. Polynucleotides encoding epitopes may be expressed independently (i.e., operably linked to a promoter functional in the vector) or may be inserted into a vaccine vector polynucleotide (i.e., a native polynucleotide or a non-native polynucleotide) that is expressed in the vector. Suitably, the vaccine vector polynucleotide encodes a polypeptide expressed on the surface of the vaccine vector such as a transmembrane protein. The polynucleotide encoding the antigenic polypeptide may be inserted into the vaccine vector polynucleotide sequence in frame to allow expression of the antigenic polypeptide on the surface of the vector. For example, the polynucleotide encoding the antigenic polypeptide may be inserted in frame into a bacterial polynucleotide in a region encoding an external loop region of a transmembrane protein such that the vector polynucleotide sequence remains in frame.

Alternatively, the polynucleotide encoding the antigenic polypeptide may be inserted into a secreted polypeptide. Those of skill in the as will appreciate that the polynucleotide encoding the antigenic polypeptide could be inserted in a wide variety of vaccine vector polynucleotides to provide expression and presentation of the antigenic polypeptide to the immune cells of a subject treated with the vaccine vector.

The concept of a common mucosal immune system predicts that induction of immunity at one mucosal surface, such as the gut, can provide immunity at another mucosal surface, such as the lung, providing a necessary link for immunity transfer throughout mucosal surfaces. Mucosal immunity may prove to be the link in fighting a complex infection in which systemic and local immunity are necessary in preventing the spread and transmission of infectious disease.

More and more experts in the field are now in agreement that mucosal exposure and generation of mucosal immunity are likely necessary to provide maximal protection against pathogens, and that gastrointestinal exposure, through mucosal vaccines, often confers protection against other mucosal (e.g., respiratory) pathogens exhibiting those epitopes.

It is also becoming increasingly more important to limit vaccine reactions experienced when the total pathogen is attenuated or inactivated and presented to the host. One possible solution is to use a protective protein or subunit of the pathogen produced by an inert vector instead of the whole pathogen. Several vaccine vectors have emerged to date, all of which have relative advantages and limitations depending on the proposed application. Bacteria, viruses, and plants represent three potential orally administered vector systems with substantial possibility of inducing mucosal immunity and a protective immune response. However, bacterial vectors have been regarded as the front runner in vectored vaccine strategies. Considerable time and research effort has been spent in the pursuit of developing effective bacterial vaccines which vector heterologous antigens.

Many *Bacillus* spp. are considered generally recognized as safe (GRAS) organisms with a very comprehensive record of safe oral consumption, widely known for their use in food fermentation processes and as probiotics. *Bacillus* bacteria, specifically *Bacillus subtilis* provide a promising alternative to the use of pathogenic bacteria as a oral vectored vaccine. Furthermore, *Bacillus* possesses intrinsic adjuvant activity potentiating stimulation of host specific immunity. These properties combined make *Bacillus* an attractive candidate for use as an oral vaccine.

A number of potential vaccine antigens have been expressed in *Bacillus* vectors and evaluated for their potential effectiveness. As with traditional vectors, researchers have shown oral live and killed (inactivated) *Bacillus* vaccine vectors expressing recombinant foreign antigens to stimulate systemic, mucosal, humoral, and cell-mediated immune responses against heterologous antigens. In addition to protection against pathogens, *Bacillus* has intrinsic probiotic properties, which increase the health of the host by stimulating the innate immune response through the toll-like receptor system, fortify the gastro-intestinal system by enhancing the production of tight junction repair proteins and down regulate the inflammatory response caused by pathogenic Gram-negative bacteria.

The epitopes selected for the vaccine candidates tested involved the adhesive proteins secreted from the micronemes. Proteolytic trimming of microneme contents occurs rapidly after their secretion onto the parasite surface and is proposed to regulate adhesive complex activation to enhance binding to host cell receptors. Microneme proteins are also critical to the motility of the protozoa as it moves towards the host cell. It has been demonstrated that protozoa which lack these proteins have a profound defect in surface processing of secreted microneme proteins. Notably parasites lack protease activity responsible for proteolytic trimming of microneme protein 2 (MIC2), microneme protein 4 (MIC4) and MIC2-associated protein (M2AP) after release onto the parasite surface. Loss of this protolytic protein decreases cell attachment and in vitro gliding efficiency leading to lower rates of invasion. Since protozoa must invade host cells to be able to carry out their replication, lower rates of invasion effects replication negatively. Thus, impacting the number of protozoa available to cause disease and be shed back into the environment. If this protein is disrupted by an immune response within the host species, the protozoa is less likely to invade host enterocytes, less likely to replicate and less likely to be able to cause disease, making this protein an excellent target for vaccination purposes.

To date there are no known commercial vaccines which have been able to meet these novel concepts and provide protection. The problem has occurred by the inability to protect proteins through the harsh environment of gastrointestinal tract without degradation until the immune system can recognize the antigen, respond accordingly, and provide protection against the intended target pathogen. This problem has been overcome with the use of a naturally occurring polysaccharide novel carrier which protects the protective protein and probiotic properties of the bacteria as it transits through the stomach and into the gastrointestinal tract.

These points offer beneficial evidence in favor of using *Bacillus* as bacteria as a subunit vector. The major benefit of using bacterial vectors is they offer mucosal routes of immunization, providing the possibility of greatly enhanced protection when compared to parenteral vaccination.

In the instant invention, VV1 is created by combining *Bacillus subtilis* with a *Bacillus* expression plasmid; this plasmid is responsible for production and transportation of the subunit, or protective protein, to the cell membrane of the *Bacillus subtilis*. The subunit produced is a highly conserved proteolytic protein critical for cell adhesion and motility of the *Eimeria*. This conserved protein is used as the immunogen/antigen for the vaccine platform and corresponds to the coding sequence of the natural protein in all Apicomplexa phylum and induces protection against Coccidiosis.

The protective protein was first characterized in *Toxoplasma gondii*. Since *Toxoplasma* and *Eimeria* are phylogenetically similar, the *T. gondii* protein sequence was entered into the National Center for Biotechnology Information (NCBI) BLASTP server to identify the orthologous protein in *Eimeria* spp. Once the protein sequence was identified, we used nucleotide codon optimization for *Bacillus subtilis* to derive the necessary nucleotide sequence for the gene sequence and a gene was synthesized (Genscript). This synthetic gene complete with the homologous restriction sites was amplified using traditional PCR with gene specific primers. The amplification product was purified by gel extraction techniques, concentrated, digested with BamHI and XbaI overnight, and re-purified. The *Bacillus* expression plasmid pHT10 was digested with BamHI and XbaI, purified, concentrated, and treated with rSAP. The digested gene insert and plasmid were then mixed into a T4 DNA ligase reaction overnight at room temperature. The ligation reaction was transformed into *E. coli* DH5a (Invitrogen) and transformants were screened for the gene insert on LB agar with ampicillin (100 μg/ml, LBAmP). The new plasmid, pCox, was purified from *E. coli* and transformed into *B. subtilis*. Transformants were selected on tryptic soy agar with chloramphenicol (5 μg/ml, $TSA^{Cm}$), creating the recombinant *Bacillus subtilis* stain, VV1.

The instant invention inserts overlapping sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or any combination thereof.

TABLE 1

Listing of the Overlapping Sequences and Their Proximity

| SEQ ID Name | Sequence |
|---|---|
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 2 | STPPPSPPAQPTPQPQPHPPPQPET |
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 3 | PPQPETPPSAPSPPPPTPPSAPSPS |
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 4 | PPPTPPSAPSPSPRTPPSAPSPSPR |
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 5 | APSPPPPTPPCAPSPSPPTPPPGSP |
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 6 | PPPPTPPCAPSPSPPTPPPGSPHKP |
| SEQ ID NO: 1 | STPPPSPPAQPTPQPQPHPPPQPETPPSAPSPPPPTPPSAPSPSPRTPPSAPSPSPR<br>APSPPPPTPPCAPSPSPPTPPPGSPHKPSPPPSPPPTESAPGAPPS |
| SEQ ID NO: 7 | SPPPSPPPTESAPGAPPS |
| SEQ ID NO: 8 | GGG<br>msgkgpaigi dlgttyscvg vfqhgkveii andqgnrttp<br>syvaftdter ligdaaknqv amnptntifd akrligrkyd dptvqsdmkh<br>wpfrvvnegg kpkvqveykg emktffpeei ssmvltkmke iaeaylgkkv<br>etavitvpay fndsqrqatk dagtitglnv mriineptaa aiaygldkkg<br>trageknvli fdlgggtfdv siltiedgif evkstagdth<br>lggedfdnrm vnrfveefkg khkrdnagnk ravrrlrtac erarrtlsss<br>tqasieidsl fegidfytsi trarfeelna dlfrgtlepv ekalrdakld<br>kgqiqeivlv ggstripkiq kllqdffngk elnksinpde avaygaavqa<br>ailmgdksen vqdllllldvt plslgietag gvmtalikrn ttiptkqtqt<br>fttysdnqss vlvqvyeger amtkdnnllg kfdltgippa<br>prgvpqievt fdidangiln vsavdkstgk enkititndk grlskddidr<br>mvqeaekyka edeanrdrvg aknslesyty nmkqtvedek lkgkisdqdk<br>qkvldkcqev issldrnqma ekeeyehkqk eleklcnpiv tklyqgagga<br>gaggsggpti<br>eevd<br>GGG |

TABLE 1-continued Listing of the Overlapping Sequences and Their Proximity

| SEQ ID Name | Sequence |
|---|---|
| SEQ ID NO: 9 | STPPPSPPAQPTPQPQPHPPPQPETSSSPPQPETPPSAPSPPPPTPPSAPSPSSSPPPTPPSA<br><br>PSPSPRTPPSAPSPSPRGGG msgkgpaigi dlgttyscvg vfqhgkveii andqgnrttp<br><br>syvaftdter ligdaaknqv amnptntifd akrligrkyd dptvqsdmkh<br>wpfrvvnegg kpkvqveykg emktffpeei ssmvltkmke iaeaylgkkv<br>etavitvpay fndsqrqatk dagtitginv mriineptaa aiaygldkkg<br>trageknvli fdlgggtfdv siltiedgif evkstagdth<br>lggedfdnrm vnrfveefkg khkrdnagnk ravrrlrtac erarrtlsss<br>tqasieidsl fegidfytsi trarfeelna dlfrgtlepv ekalrdakld<br>kgqiqeivlv ggstripkiq kllqdffngk elnksinpde avaygaavqa<br>ailmgdksen vqdlllldvt plslgietag gvmtalikrn ttiptkqtqt<br>fttysdnqss vlvqvyeger amtkdnnllg kfdltgippa<br>prgvpqievt fdidangiln vsavdkstgk enkititndk grlskddidr<br>mvqeaekyka edeanrdrvg aknslesyty nmkqtvedek lkgkisdqdk<br>qkvldkcqev issldrnqma ekeeyehkqk eleklcnpiv tklyqgagga<br>gaggsggpti<br><br>eevdGGG APSPPPPTPPCAPSPSPPTPPPGSPSSSPPPPTPPCAPSPSPPTPPPGSPHKPSSS<br><br>SPPPSPPPTESAPGAPPS |

Table 1 illustrates how SEQ ID NOs: 2 through 7 combine and overlap to form SEQ ID NO: 1. SEQ ID NO: 8 is an immunostimulation molecule of the insertion protein sequence. The larger sequence of SEQ ID NO: 1 is broken down into smaller epitopes to allow for maximum immune recognition and stimulation in the inoculated specimen. SEQ ID NO: 9 is the insertion protein sequence where the smaller epitopes of SEQ ID NOs: 2 through 7 surround the immunostimulation molecule of SEQ ID NO: 8 and the GGG and SSS are used to produce immunological inert codon to separate the epitopes into easily scanned frames for the immune system of the inoculated specimen.

The protective subunit is produced during fermentation of VV1 at between 28 and 37° C. and induction with 0.5 m M IPTG. The culture is inactivated with formalin. To produce the Test Vaccine and iterations thereof, the inactivated VV1 culture was mixed with a naturally occurring polysaccharide, methyl cellulose (encapsulation media); which acts as the vehicle to protect the vaccine as it passes through the gastrointestinal tract.

In the preliminary immunological and efficacy trial, a single "high" concentration of protective antigen was used. In the first validation Clinical Trial, two vaccine formulations were tested, Test Vaccine 1 (TV1, low antigen concentration) and Test Vaccine 2 (TV2, high antigen concentration, same as in preliminary efficacy trial). In Clinical Trial 2 and 3, Test Vaccine 2 was used and compared against a non-treated group and/or a USDA licensed commercial vaccine (Coccivac-B52).

The instant invention includes a vaccine vector, as described above, comprising a first polynucleotide encoding the antigenic polypeptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or any combination thereof. The instant invention also includes a vaccine vector, as described above, comprising a first polynucleotide encoding the antigenic polypeptide selected from the group consisting of SEQ ID NO: 1, SEQ ID NO: 8, SEQ ID NO: 9, or any combination thereof. The instant invention utilizes a novel approach by inserting polynucleotide sequences encoding non-native linear epitopes (antigenic polypeptides). The antigenic polypeptides may be used in combination with an immunostimulatory polypeptide known in the art in the vaccine vector. The antigenic polypeptide and the immunostimulatory polypeptide are suitably not polypeptides found natively associated with the vector. The epitope or antigenic polypeptide and the immunostimulatory polypeptide may be expressed on the surface of recombinant vectors.

The instant invention may include a pharmaceutical composition comprising the vaccine vector described above and a pharmaceutically acceptable carrier. A pharmaceutically acceptable carrier is any carrier suitable for in vivo administration. The pharmaceutically acceptable carrier may include any carrier known in the art including, but not limited to, water, buffered solutions, glucose solutions or bacterial culture fluids. Additional components of the compositions may suitably include excipients such as stabilizers, preservatives, diluents, emulsifiers, and lubricants. Examples of pharmaceutically acceptable carriers or diluents include stabilizers such as carbohydrates (e.g., sorbitol, mannitol, starch, sucrose, glucose, dextran), proteins such as albumin or casein, protein containing agents such as bovine serum or skimmed milk and buffers (e.g., phosphate buffer). Especially when such stabilizers are added to the compositions, the composition is suitable for freeze drying or spray-drying.

The instant invention further includes a method of enhancing the immune response against an Apicomplexan parasite in a subject comprising administering to the subject the vaccine vector as described herein in an amount effective to enhance the immune response of the subject to the Apicomplexan parasite. The Apicomplexan parasite is selected from the group consisting of *Eimeria, Plasmodium, Toxoplasma*, and *Cryptosporidium*. The vaccine vector is administered by a method including oral, intranasal, parenteral, in ovo or any other method known in the art. The method results in an immune response which includes an antibody response.

Enhancing an immune response includes, but is not limited to, enhancing antibody responses. Suitably the IgA response is enhanced, more suitably the secretory IgA response is enhanced after administration of the vaccine vector as compared to a control. The control may be the same subject prior to administration of the vector, a comparable subject administered a vaccine vector alone or a vector expressing an irrelevant or a non-Apicomplexan antigenic polypeptide. The antibody response, suitably the IgA response, may be increased as much as two-times, three-times, four-times, five-times or more as compared to the response of a control subject. The enhanced immune response may also result in a reduction of the ability of Apicomplexan to grow or replicate and colonize the subject after administration of the vectors described herein. Such a reduction may be tested by challenging a subject administered the vector with an Apicomplexan infestation and monitoring the ability of the parasite to colonize and replicate within the subject as compared to a control subject. This may be measured by a decrease in the number of oocysts per gram of fresh fecal material (see Figures below).

Figure 1:
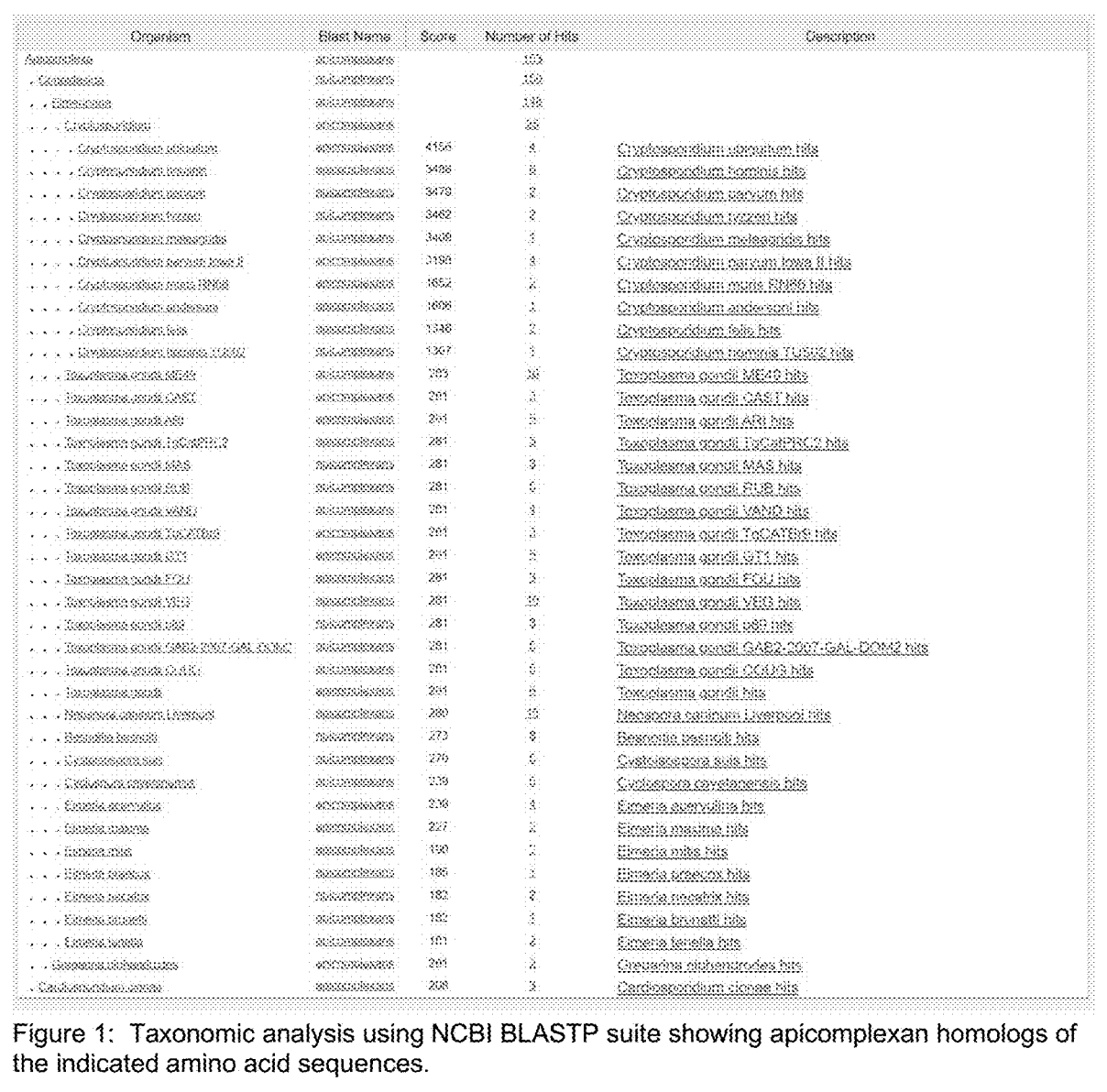
Figure 2B:
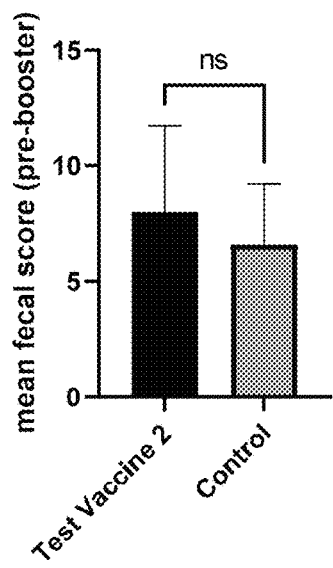
FIG. 2B is a bar graph showing the mean and SD fecal score for study days 1-15
Figure 2C:
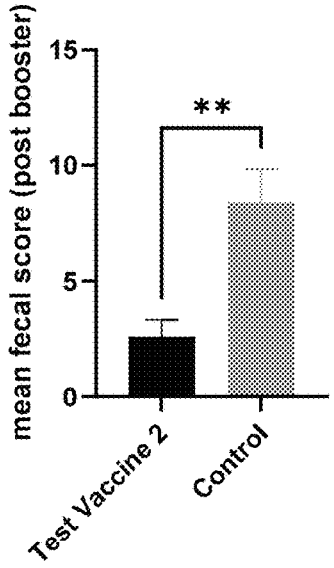
FIG. 2C is a bar graph showing the mean and SD fecal score for study days 16-20.

The antigen of this present vaccine is conserved across the Apicomplexa phylum (FIG. 1) and induces protective immunity in a wide range of hosts, including, but not limited to, chickens and cattle. A preliminary clinical trial was carried out to determine vaccine efficacy against *Cryptosporidium* induced diarrhea in Argentina. The tropical wet season (April-May) coincides with the calving season in the Province of Buenos Aires, Argentina and is associated with increased occurrences of diarrhea from *Cryptosporidium* ssp. infections. To test the efficacy of this Test Vaccine 2 against *Cryptosporidium* associated diarrhea, two independent dairy farms were utilized in this area of Argentina. Calves born within a 24-48-hour period of the trial start day on these two dairy farms were ear tagged and alternately assigned to the Vaccine (n=11) or Control group (n=9) and given a 5 ml dose of Test Vaccine 2 or saline, respectively. On day 15 of the study (calf day of life 13-15), each group was administered a second 5 ml dose of Test Vaccine 2 or saline, respectively. Each day from birth through study day 20, the feces of each calf enrolled in the study was observed and scored (FIG. 2A). Fecal scoring was as follows: 0 (normal), 1 (pasty), 2 (liquid). Any calf with a score greater than zero was considered to have diarrhea in this study. Prior to the second treatment dose administration, the mean daily fecal score were similar among the two groups (FIG. 2B). Subsequently, on the study days after the 2nd treatment dose administration (15 d, booster), days 16-20, the mean fecal score for the Vaccine group was significantly lower (FIG. 2C). These data support the claim that this present invention, Test Vaccine 2, prevents disease associated with the apicomplexan phyla in a wide range of hosts.

Any method described herein may incorporate any design element contained within this application and any other document/application incorporated by reference herein.

The following examples are meant only to be illustrative and are not meant as limitations on the scope of the invention or of the appended claims.

EXAMPLES

Animal Studies

*Eimeria* dose titration and immunological response studies and the preliminary efficacy trial were conducted at Vetanco Research and Development (Buenos Aires, Argentina) and all animal handling procedures were in compliance with The National Agricultural Technology Institute (INTA-Argentina) guidelines. Three validation trials were conducted by Southern Poultry Research, Inc (SPR, Athens, Ga.) and in accordance with United States Department of Agriculture animal welfare guidelines and SPR's IACUC board.

Title:

*Eimeria* dose titration and preliminary efficacy study of Test Vaccine.

*Eimeria* Dose Titration

*Eimeria maxima* (EM) oocysts were propagated in vivo according to previously published methods. A preliminary dose titration study was carried out, offset by 1 week, to determine the *Eimeria* challenge selection for the preliminary efficacy study. Briefly, ten 14 day (d) old Cobb 500 broilers were weighed, divided into three groups and challenged with three different doses of sporulated oocysts of EM by oral gavage. A fourth group of chicks were sham challenged with saline. One-week post-challenge, body weight (BW), body weight gain (BWG) and lesion scores were determined. Based on the criterion that the challenge dose caused a 30-35% depression in weight gain when compared to saline-challenged controls, a single dose was chosen (data not shown).

In the preliminary efficacy study, 120 day-of-hatch Cobb 500 broiler chicks were obtained from a local commercial hatchery and neck-tagged and randomly assigned to one of three treatment groups (n=40/pen):

| Treatment |
| --- |
| 1. Control, saline only |
| 2. Excipient only, no antigen |
| 3. Test vaccine (TV) |

On 3 d post hatch, all chicks in group 1 were sham vaccinated via oral gavage, with 0.20 mL/chick of saline and chicks in group 2 were given the same volume of a solution containing only excipient (encapsulation media) via oral gavage. Chicks in treatment group 3 were inoculated, via oral gavage, with 0.20 mL/chick of Test Vaccine (TV). On 14 d post-hatch birds were boosted with the same treatment they received on Day 3. At 21 d post-hatch, all chickens were weighed and orally challenged with $1 \times 10^4$ sporulated oocysts of EM/chick and all treatments were co-mingled in a single, large pen.

The experiment was terminated at 28 d post-hatch and all chickens were weighed before termination and intestinal macroscopic lesions evaluated as per the standard Johnson-Reid scale. The scoring pattern was as follows:

0—no lesions

1—mild lesions with faint red petechiae on the mucosa

2—moderate lesions with extensive petechiae formation, general redness of mucosa and thickened intestinal wall 3—severe lesions with slime formation, orange mucus and inflammation, and 4—hemorrhagic lesions with increased slime formation, reddish mucus and thickened mucosa.

Furthermore, blood samples were collected from 10 chickens per treatment group on 21 d post hatch before challenge and the serum was used for determining antigen-specific systemic IgG antibody response. Additionally, a section of ileum was collected from 10 chickens per treatment group on 28 d post hatch. These ileum samples were used to harvest the mucosal layer of the gastrointestinal tract to determine antigen-specific secretory IgA antibody response to the vaccine subunit.

Determination of Antigen-Specific IgG and Secretory IgA Antibodies by ELISA

Serum collected from birds in the immunization study was used in an ELISA to determine relative antibody responses. Briefly, individual wells of a 96-well plate were coated with the synthetic subunit. Antigen adhesion was allowed to proceed overnight at 4° C., the plates were then washed and blocked with a ELISA blocking buffer for 1 hour at room temperature. Plates were then incubated for 2 hours with a 1:50 dilution of the previously collected sera. The plates were rinsed again followed by incubation with a Peroxidase-labeled anti-chicken IgG secondary antibody (Jackson Immuno Laboratories—West Grove, Pa., USA) for an additional hour. After subsequent rinsing, the plates were developed using a peroxidase substrate kit (BD OptEIA-Fisher Scientific—Waltham, Mass., USA) and absorbances were read on a spectrophotometer at 450 nm. Each plate contained a positive control and negative control where a pooled sample from vaccinated chicks and pre-immune chicken serum, respectively, replaced the serum from the treatment groups. The absorbance obtained for the positive control, negative control and experimental samples were used to calculate Sample to Positive control ratios (S/P ratios) using the following calculation: (sample mean−negative control mean)/(positive control mean−negative control mean). The ELISA method used for detection of sIgA was similar to the above described assay for serum immunoglobulin except we used goat anti-chicken IgA conjugated with horseradish peroxidase (GenTex) in place of the anti-chicken IgG antibody conjugate.

Results

Chick body weight gain (BWG) was evaluated with regard to vaccine candidate efficacy. Body weights in all groups were similar on the day of challenge (day 21-, data not shown), however, in the second part of the trial, chickens vaccinated with Test Vaccine gained significantly more weight (116.43 grams) during the challenge period (p<0.05) as compared to saline and excipient administered chicks in the presence of an *Eimeria* challenge (Table 2). The challenge dose caused a 7.5% mortality in the saline sham-vaccinated challenged group (Table 2) in a challenge period. While coccidiosis lesions were seen in all groups by day 28 when lesions were evaluated, no differences were observed in the severity of lesions between treatment groups (Table 2). In most situations, lesion scores have not been well correlated with the protective effects of vaccines. This may be due to immunopathology in the vaccinated broilers causing interference with the ability to accurately determine lesion scores. As a matter of fact, what one sees as lesions in immunized chicks may actually be the process of recovery and tissue regeneration. Therefore, histopathological analysis of tissue samples by differential staining may be a more accurate method for understanding gross pathology rather than relying on macroscopic lesions.

Additionally, subunit specific antibody responses (FIG. 3) were observed both locally and systemically (sIgA and IgG) confirming our belief that vectored subunits presented to the immune system in a recognizable fashion can induce protection. As seen in this experiment, the Test Vaccine was able to markedly reduce aspects of disease caused by an *Eimeria maxima* (EM) challenge, namely, a reduction in weight gain. Further studies will be necessary to evaluate the ability of the Test Vaccine to offer cross protection against other species of *Eimeria*, majorly *E. tenella* and *E. acervulina*, because these two species along with EM have been considered most important in the commercial industry.

TABLE 2

Body Weight Gain (BWG), lesion scores, and percent mortality in broilers immunized with subunit vaccines candidates against coccidiosis from preliminary feasibility trial.

| Treatments | BWG (D21-28) | Lesion Score | Percent Mortality |
|---|---|---|---|
| Saline | $294.49 \pm 26.50^b$ | $1.8 \pm 0.1^{bc}$ | 3/40 (7.5%) |
| Excipient | $339.38 \pm 28.77^b$ | $2.5 \pm 0.1^a$ | 1/40 (2.5%) |
| Test Vaccine | $410.92 \pm 19.02^b$ | $2.0 \pm 0.2^{ab}$ | 2/40 (5%) |

BWG (g) and lesion scores expressed as means ± standard error. All chicks were orally gavaged with the respective treatment at day 3 and day 14 of life and *Eimeria* challenge was performed at 21 d of age. BWG was evaluated during the challenge period. Mortality expressed as percentage of death/total chickens.
$^{a,b,c}$Means with different letters within the same column indicate difference (p < 0.05).

Clinical Trials

Each validation clinical trial utilized the Cobb 500 strain broiler chicken. Day-of-hatch birds received routine vaccinations (no coccidia vaccines). No birds were replaced during the trials. Environmental conditions were monitored during each trial and were appropriate to the age of the animals. Fresh clean litter was provided to all animals throughout the duration of each trial. Water and feed were provided ad libitum and all feed was fed as crumbles/pellets and absent any anticoccidial. In trials where feed intake was monitored the following schedule was used: Day 0 to 20, starter feed; Day 21 to 34, grower feed; Day 35 to 42, finisher feed. All feed was weighed by pen and recorded. At the end of each feeding schedule, non-consumed feed was weighed and record. Where indicated, productive parameters (Feed Intake, Adjusted Feed Conversion Rate and Average Weight Gain) were measured throughout the course of the trials. When measured, intestinal lesion scores were assessed as a measure of coccidial damage.

Upon initiation of each validation clinical trial, fifty male chicks were allocated to each treatment pen by blocks (30 pens, 10 blocks, randomized within blocks of three pens each) (Cobb-Vantress hatchery, Cleveland, Ga.). Chicks were randomly and equally assigned to each group. In the first validation Clinical Trial, two vaccine formulations were tested, Test Vaccine 1 (TV1, low antigen concentration) and Test Vaccine 2 (TV2, high antigen concentration, same as in preliminary efficacy trial). In Clinical Trial 2 and 3, Test Vaccine 2 was used and compared against a non-treated group and/or a USDA licensed commercial vaccine (Coccivac-B52). Administration of experimental vaccines was by oral gavage (0.2 ml/bird) on D2 and D16. Coccivac-B52 (Merck Animal Health—New Jersey, USA) was administered according to the manufacturer's instructions. Bird weights (kg) by pen were recorded at study initiation, Day 21, 35, and termination (Day 42).

To evaluate the level of coccidiosis immunity, on Day 21, coccidial oocyst inoculation procedures were performed as described. Briefly, on Day 21 of the study all birds received a mixed *E. acervulina, E. maxima,* and *E. tenella* coccidia inoculum. The inoculum was mixed into the feed found in the base of each pen's tube feeder. For each study, when indicated, five birds from each pen were selected, sacrificed, weighed, and examined for the degree of presence of coccidia lesions using the Johnson-Reid scoring method. Additionally, when indicated, fresh fecal samples were collected from each pen. These representative samples were tested to determine the degree of oocysts shedding/cycling (oocysts/gram of fecal matter).

Statistical Analysis

Body weight (BW), body weight gain (BWG) and lesion score data from the studies were subjected to ANOVA using JMP7 (SAS institute, Cary, N.C.), partitioned and treatment means were deemed significant if the p-value was less than or equal to 0.05 (p 0.05). Mortality data were compared using the chi-square test of independence testing all possible group combinations to determine significance.

Example 1 (Clinical Trial 1)

Title

Comparison of the performance and level of coccidial immunity of broiler chickens vaccinated with a test coccidia vaccine.

Study Objectives

The objective of this study is to determine the effects on performance of a Test Coccidia Vaccine 1 and 2. Degree of acquired coccidial immunity will also be compared.

Description of the Treatments

The experiment will consist of 30 pens starting with 50 broiler chickens. The treatments will be replicated in ten blocks, randomized within blocks of three pens each.

| Treatment |
| --- |
| 1. No Vaccine |
| 2. Test Vaccine 1 (TV1, low antigen concentration) |
| 3. Test Vaccine 2 (TV2, high antigen concentration) |

Vaccines will be orally gavaged (0.2 ml/bird) individually on Days 2 and 16.

Floor Pen Description and Management

A diagram of the test facility will be included. The test house is divided into pens of equal size, arranged along a central aisle. Subtracting out for equipment, the initial bird density will be ~0.73 square ft/bird. Each pen has 5 feet high side walls with bottom 1½ feet being of solid wood to prevent bird migration. The pens will be prepared for use in the study according to SPR SOP. All flooring of each pen will have approximately 4 inches of clean litter.

The temperature of the building will be monitored. Environmental conditions during the trial (temperature) will be appropriate (optimum) to the age of the animals. Illumination will be provided by fluorescent bulbs placed above the pens. The lighting scheme will be 21 hours of light per day.

The diets will be provided ad libitum in one tube-type feeder per pen. From day 1 until day 7, feed will also be supplied on a tray placed directly on the litter of each pen.

Standard floor pen management practices will be used throughout the experiment. Animals and housing facilities will be inspected twice daily, observing and recording the general health status, constant feed and water supply as well as temperature, removing all dead birds, and recognizing unexpected events.

Diets

All feeds will be fed as crumbles/pellets. All feeds will not contain any anticoccidial drug, however all feeds will contain BMD 50 g/t.

All feed will be weighed by pen. Starter feed will be fed from Day 0 to 21. On Day 21, non-consumed starter will be weighed and discarded. Grower feed will be issued and fed until Day 35. On Day 35, non-consumed grower will be weighed and discarded. Finisher feed will be issued and fed until Day 42. On Day 42, non-consumed finisher will be weighed and discarded.

Birds

Day of hatch male chicks will be obtained from Cobb-Vantress hatchery, Cleveland, Ga. The strain will be Cobb 500. Breeder flock will be recorded. 2000 chicks will be allocated to the study. At the hatchery, the birds will receive routine vaccinations (no coccidia vaccines). The birds will be sexed at the hatchery. Only healthy appearing chicks will be used in the study. At study initiation fifty males will be allocated to each treatment pen by blocks. Vaccines will be applied orally at a recommended commercial dose (0.2 ml/chick). No birds will be replaced during the course of the study. Number and disposition of all birds not used for allocation will be documented. Bird weights (kg) by pen will be recorded at study initiation, Day 21, 35, and termination (Day 42).

Birds found dead during the study will be noted on the Daily Mortality Record, and will not be replaced. Pen number, the date of mortality, sex, weight, and diagnosis will be recorded.

Coccidial Challenge

To evaluate the level of coccidiosis immunity, on Day 21, Coccidial oocyst inoculation procedures are described in SPFR SOP. On Day 21 of the study all birds received a mixed *E. acervulina, E. maxima*, and *E. tenella* coccidia inoculum. The inoculum was mixed into the feed found in the base of each pen's tube feeder.

Coccidia Intestinal/Cecal Lesion Scoring

On Day 27, five birds from each pen were selected, sacrificed, weighed, and examined for the degree of presence of coccidia lesions. The Johnson and Reid, 1970 method of coccidiosis lesion scoring was used to score the infected region(s) of the intestine. The scoring was based on a 0 to 4 score, with 0 being normal and 4 being the most severe.

Coccidia Oocysts Per Gram Litter

On Days, 28, 35, and 42 fresh fecal samples were collected from each pen. These representative samples will be tested to determine the degree of oocysts shedding/cycling. Oocysts per gram (opgs) will be determined for each sample.

Data Entry and Analysis

Source data will be entered with indelible ink. Entries will be legible, signed or initialed, and dated by the person making the observation entry. Each sheet of source data will be signed by the person(s) attributed to the data. Any mistake or change to the source data will be initialed and dated and a correction code or statement added as to why the change was made.

For Day 0-21, 0-35, and 0-42, means for pen weight gain, feed consumption, FCR, mortality, opgs, and coccidia lesion scores will be calculated.

Results:

Productive parameters (Feed Intake, Adjusted Feed Conversion Rate and Average Weight Gain) were measured throughout the course of the experiment (Table 3 and FIG. 4). Data show that at day 21, Test Vaccine 2 had a slight reduction in weight gain when compared to the other treatment groups presumably due to intensity of immune response generated by vaccine administration at days 2 and 16; however, feed intake and FCR was unaffected between treatment groups. Day 35 data show that statistically there is no difference between treatment groups for Average Weight Gain. Productive parameters differences occur in improved adj FCR for the group treated with Test Vaccine 2 and measured in the intermediate period 1 week after coccidia challenge. By the termination of the experiment, Day 42, statistically there was no difference in Avg Weight Gain; however, numerically there was a 19 gram difference per bird when comparing Test Vaccine 2 with the non-treated controls this difference amounts to an increase in total weight of 9.5 kg for the Test Vaccine 2 group over the non-treated control group. There was no difference in feed intake, but the Test Vaccine 2 group had improved feed efficiency as evidenced by the improved adj FCR.

TABLE 3

Feed intake, Adjusted Food Conversion Rate (Adj. FCR) and Average Pen Weight Gain (Avg. Wt. Gain) in male broilers immunized with subunit vaccines candidates against coccidiosis from the first clinical trial.

| Day | Treatments | Feed Intake | Adj. FCR | Avg. Wt. Gain (kg) |
|---|---|---|---|---|
| 21 | No vaccine | 42.52$^a$ | 1.489$^a$ | 0.557$^{ab}$ |
|    | Test Vaccine 1 | 42.04$^{ab}$ | 1.474$^a$ | 0.557$^{ab}$ |
|    | Test Vaccine 2 | 40.08$^b$ | 1.460$^a$ | 0.535$^b$ |
| 35 | No vaccine | 123.11$^{ab}$ | 1.663$^a$ | 1.579$^a$ |
|    | Test Vaccine 1 | 123.26$^{ab}$ | 1.661a | 1.585$^a$ |
|    | Test Vaccine 2 | 119.27$^b$ | 1.623b | 1.578$^a$ |
| 42 | No vaccine | 164.82$^a$ | 1.734$^a$ | 2.118$^a$ |
|    | Test Vaccine 1 | 165.62$^a$ | 1.727$^{ab}$ | 2.141$^a$ |
|    | Test Vaccine 2 | 162.15$^a$ | 1.704$^b$ | 2.137$^a$ |

All chicks were immunized with the respective treatment at day 2 and day 16 of life and Eimeria challenge was performed at 21 d of age. Production parameters were measured throughout the course of the trial.
$^{a,b,c}$Means with different letters within the same column indicate difference (p < 0.05).

Lesion scores on Day 34 (Johnson and Reid, 1970) were assessed as a measure of coccidial damage (E. acervulina, E. maxima, E. tenella and total average) to the gastrointestinal tract (Table 4). Chickens vaccinated with Test Vaccine 2 had significantly lower lesion scores for all three Eimeria species and in total average lesion scores when compared to the non-treated controls. Average lesion scores were reduced by 42% in the Test Vaccine 2 group as compared to the non-treated controls; percent reduction in lesion scores for the individual Eimeria species between Test Vaccine 2 and non-treated control groups were as follows: EA 36%, EM 43% and ET 60%.

TABLE 4

Coccidial Lesion Scores in the Gastrointestinal Tract for Eimeria acervulina (EA), Eimeria maxima (EM), Eimeria tenella (ET) and total average lesion scores (AVG). Different letters indicated statistical significance between treatments (p ≤ 0.05).

| Treatments | EA | EM | ET | AVG |
|---|---|---|---|---|
| 1. No Vaccine | 2.34a | 1.140a | 0.900a | 1.46a |
| 2. Test Vaccine 1 | 1.62b | 0.900ab | 0.720a | 1.08b |
| 3. Test Vaccine 2 | 1.52b | 0.660b | 0.360b | 0.85c |

Additionally, on Days 28, 35 and 42 fresh fecal matter was collected from each experimental pen individually to determine coccidial shedding: Oocysts per gram of fecal matter (OPG) for each individual Eimeria spp and total oocyst counts (Table 5 and FIG. 4). Data generated from these analyses show total oocyst counts/gram of fecal matter for the group treated with Test Vaccine 2 had a statistically significant initial 42% reduction (directly correlated to lesion scores reported above) in OPG counts at day 28 (FIG. 4B) and a subsequent statistically significant 83% reduction in OPG at both days 35 (FIG. 4C) and 42 (FIG. 4D) when compared to the non-treated control group. These data indicate that the protozoa is not replicating and is simply transient. This statement is further backed up by individual Eimeria oocyst counts at days 35 and 42 in which Eimeria maxima oocyst counts went to 0 at day 35 and remained there until the conclusion of the experiment in the Test Vaccine 2 group and Eimeria acervulina and Eimeria tenella oocyst counts are both approaching zero by the termination of the experiment in the Test Vaccine 2 group.

TABLE 5

Coccidial Shedding Counts (oocysts per gram of fresh fecal material, OPG) for Eimeria acervuline (EA), Eimeria maxima (EM), Eimeria tenella (ET) and total average oocysts counts (Total). Different letters indicated statistical significance between treatments (p ≤ 0.05).

| Treatments | Eimeria acervulina | Eimeria maxima | Eimeria tenella | Total |
|---|---|---|---|---|
| OPGs Day 28 | | | | |
| 1. No Vaccine | 2891a | 1037a | 220a | 4149a |
| 2. Test Vaccine 1 | 3335a | 1227a | 240a | 4802a |
| 3. Test Vaccine 2 | 1714ab | 334a | 367a | 2415b |
| OPGs Day 35 | | | | |
| 1. No Vaccine | 594ab | 313a | 987a | 1894a |
| 2. Test Vaccine 1 | 460ab | 0b | 233a | 694ab |
| 3. Test Vaccine 2 | 240b | 0b | 87a | 327b |
| OPGs Day 42 | | | | |
| 1. No Vaccine | 360a | 153a | 93a | 607a |
| 2. Test Vaccine 1 | 107b | 13b | 47b | 167b |
| 3. Test Vaccine 2 | 67b | 0b | 40b | 107b |

Example 2 (Clinical Trial 2)

Title

Comparison of the performance and level of coccidial immunity of broiler chickens vaccinated with a test coccidia vaccine (Test Vaccine 2).

Study Objectives

The objective of this study is to determine the effects on performance of a Test Coccidia Vaccine 2. Degree of acquired coccidial immunity will also be compared.

Materials and Methods

The experimental design and methods were kept consistent with Example 1 (see previous): with the exception that only Test Vaccine 2 was used for Example 2 and compared to a non-vaccine control and oocysts per gram were only determined on Day 27 instead of the three time points as in the previous experiment.

Results:

Productive parameters (Feed Intake, Adjusted Feed Conversion Rate and Average Weight Gain) were measured throughout the course of the experiment (Table 6). Data show that at day 21 (Table 6) the Test Vaccine 2 had a slight numerical reduction in weight gain when compared to the non-treated group presumably due to intensity of immune response generated by vaccine administration at days 2 and 16; however, statistically average weight gain, feed intake and FCR were no different than the non-treated control (Table 6). Day 35 data show that there is a statistical difference between the Test Vaccine 2 group and the non-treated control group for FCR and DWG presumably due to the increased intensity of the challenge from experiment 1. Day 42, again statistical differences were observed in DWG and FCR when comparing Test Vaccine 2 group with the non-treated controls with the vaccinated birds weighing an average of 155 g each more than the non-treated control birds.

Lesion scores on Day 34 (Johnson and Reid, 1970) were assessed as a measure of coccidial damage (E. acervulina, E. maxima, E. tenella and total average) to the gastrointestinal tract (Table 7 and FIG. 5A). Chickens vaccinated with the Test Vaccine 2 had significantly lower lesion scores for all three Eimeria species and in total average lesion scores when compared to the non-treated controls. Average lesion scores were reduced by 45% in the Test Vaccine 2 group as compared to the non-treated controls; percent reduction in lesion scores for the individual *Eimeria* species between the Test Vaccine 2 group and non-treated control groups were as follows: EA 39%, EM 39% and ET 66%.

Additionally, on Day 28, fresh fecal matter was collected from each experimental pen individually to determine coccidial shedding: Oocysts per gram of fecal matter (OPG) for each individual *Eimeria* spp. and total oocyst counts (Table 8 and FIG. 5B). Data generated from these analyses show total oocyst counts/gram of fecal matter the group treated with the Test Vaccine 2 had a statistically significant 65% reduction. Statistically significant reductions were also seen in each individual strain: EA 75%, EM 85% and ET 40% when comparing the Test Vaccine 2 against the non-treated control group.

TABLE 6

Feed intake, Adjusted Food Conversion Rate (Adj. FCR) and Average Pen Weight Gain (Avg. Wt. Gain) in male broilers immunized with subunit vaccines candidates against coccidiosis from the second clinical trial.

| Day | Treatments | Feed Intake | Adj. FCR | Avg. Wt. Gain (kg) |
|---|---|---|---|---|
| 21 | No vaccine | $48.94^a$ | $1.367^a$ | $0.684^a$ |
|  | Test Vaccine 2 | $47.81^a$ | $1.368^a$ | $0.665^a$ |
| 35 | No vaccine | $139.31^a$ | $1.986^a$ | $1.428^b$ |
|  | Test Vaccine 2 | $137.28^a$ | $1.826^b$ | $1.546^a$ |
| 42 | No vaccine | $197.55^a$ | $2.133^a$ | $1.948^b$ |
|  | Test Vaccine 2 | $196.08^a$ | $1.985^b$ | $2.103^a$ |

All chicks were immunized with the respective treatment at day 2 and day 16 of life and *Eimeria* challenge was performed at 21 d of age. Production parameters were measured throughout the course of the trial.
$^{a,b,c}$Means with different letters within the same column indicate difference (p < 0.05).

TABLE 7

Coccidial Lesion Scores in the Gastrointestinal Tract for *Eimeria acervulina* (EA), *Eimeria maxima* (EM), *Eimeria tenella* (ET) and total average lesion scores (AVG). Different letters indicated statistical significance between treatments (p ≤ 0.05).

| Treatments | *Eimeria acerv.* | *Eimeria maxima* | *Eimeria tenella* | Avg. |
|---|---|---|---|---|
| 1. No Vaccine | 2.44a | 2.16a | 1.38a | 1.99a |
| 2. Test Vaccine 2 | 1.51b | 1.33b | 0.47b | 1.10b |

TABLE 8

Coccidial Shedding Counts (oocysts per gram of fresh fecal material) for *Eimeria acervuline* (EA), *Eimeria maxima* (EM), *Eimeria tenella* (ET) and total average oocysts counts (Total). Different letters indicated statistical significance between treatments (p ≤ 0.05).

| Treatments | *Eimeria acerv.* | *Eimeria Maxima* | *Eimeria tenella* | Total |
|---|---|---|---|---|
| 1. No Vaccine | 13817a | 2859a | 8174a | 24850a |
| 2. Test Vaccine 2 | 3447b | 454b | 4921a | 8822b |

Example 3 (Clinical Trial 3)

Title

Comparison of the performance and level of coccidial immunity of broiler chickens vaccinated with a test coccidia vaccine (Test Vaccine 2) and compared to a commercial vaccine.

Study Objectives

The objective of this study is to determine the effects on performance of a Test Coccidia Vaccine 2 vs a commercially available coccidia vaccine.

Materials and Methods

The experimental design and methods were similar with Example 1 (see previous): with the exception that Test Vaccine 2 and a commercially available coccidia vaccine was used for Example 3 and compared to a non-treated control. The harshness of the challenge was more consistent with Example 2 as compared to the lighter challenge of Example 1. Additionally, only productivity parameters were assessed as a measure of vaccine performance due to the correlation between damage and reduction of production parameters.

TREATMENTS
Treatment*

1. No Treatment
2. Coccivac-B52*
3. Test Vaccine 2**

*Vaccine was water spray applied at SPFR prior to placement (Day 0)
**Vaccine was orally gavaged (0.2 ml/bird) individually on Days 2 and 16.

Results:

Productive parameters (Feed Intake, Adjusted Feed Conversion Rate and Average Weight Gain) were measured throughout the course of the experiment. Data show that at day 21 (Table 9) the Test Vaccine 2 had a slight numerical increase in weight gain when compared to the commercial vaccine group and the non-treated group; however, statistically average weight gain, feed intake and FCR were no different than the commercial vaccine group nor the non-treated control (Table 9). Day 35 (Table 9) data show that there is numerical difference but not a statistical difference between the Test Vaccine 2 group, the commercial vaccine group, and the non-treated control group for DWG. The test vaccine 2 group and the commercial vaccine group are statistically different from the non-treated control group in both FCR and FI. Day 42 (Table 9), statistical differences were observed in DWG and FCR when comparing the Test Vaccine and the commercial vaccine group with the non-treated controls; with the test vaccinated birds weighing an average of 87 g each more than the non-treated control birds and improving feed conversion by 84 points and numerically improved feed conversion over the commercial vaccine.

TABLE 9

Feed intake, Adjusted Food Conversion Rate (Adj. FCR), Average Pen Weight Gain (Avg. Wt. Gain), and mortality in male broilers immunized with Test Vaccine 2 or Coccivac-B52 against coccidiosis from the third clinical trial.

| Day | Treatments | Feed Intake | Adj. FCR | Avg. Wt. Gain (kg) | Percent Mortality |
|---|---|---|---|---|---|
| 21 | No vaccine | $43.28^a$ | $1.524^a$ | $0.548^a$ |  |
|  | Coccivac-B52 | $43.67^a$ | $1.522^a$ | $0.540^a$ |  |
|  | Test Vaccine 2 | $43.63^a$ | $1.520^a$ | $0.552^a$ |  |
| 35 | No vaccine | $122.33^a$ | $1.673^a$ | $1.491^b$ |  |
|  | Coccivac-B52 | 126.71 | $1.610^b$ | $1.564^a$ |  |
|  | Test Vaccine 2 | 122.94 | $1.597^b$ | $1.553^a$ |  |
| 42 | No vaccine | $167.24^a$ | $1.726^b$ | $1.995^b$ | $5.8^a$ |
|  | Coccivac-B52 | $174.99^a$ | $1.659^b$ | $2.120^a$ | $3.1^a$ |
|  | Test Vaccine 2 | $167.92^a$ | $1.642^b$ | $2.082^a$ | $3.7^a$ |

Mortality expressed as percentage of death/total chickens.
$^{a,b,c}$Means with different letters within the same column indicate difference (p < 0.05).

Overall Results

Preclinical Immunization and Efficacy Study

BW was evaluated prior to challenge and one-week post-challenge. All groups began with uniform body weights on the day of challenge (data not shown). Beneficial effects on performance after EM challenge were observed with a significant increase in BWG (p<0.05) in the group immunized with Test Vaccine when compared to the control, challenged chickens (Table 2) or the chickens administered only the excipient. No significant differences were observed in lesion scores or mortality between individual treatments.

Serum samples collected on 21 d post-hatch were used to determine subunit specific IgG antibodies. The group vaccinated with Test Vaccine showed significantly higher antibody levels than in the control or excipient only treated groups (FIG. 3). Similar results were observed in the increased levels of subunit specific secretory IgA antibodies when directly measured in the mucosal layer of the intestine (FIG. 3). These data indicate that subunit in the Test Vaccine was able to illicit significant and specific immune responses both locally and systemically which were not observed in either of the two non-vaccinated groups.

Clinical Trial 1 (Example 1)

Data show that at day 21 (Table 3) Test Vaccine 2 (previously termed Test Vaccine) had a slight reduction in weight gain when compared to the other treatment groups presumably due to intensity of immune response generated by vaccine administration at days 2 and 16; however, feed intake and FCR was unaffected between treatment groups (Table 3). Day 35 (Table 3) data show that statistically there is no difference between treatment groups for Average Weight Gain. Productive parameters differences occur in improved adjusted FCR for the group treated with Test Vaccine 2 and measured in the intermediate period 1 week after coccidia challenge. By the termination of the experiment, Day 42 (Table 3), statistically there was no difference in Avg Weight Gain; however, numerically there was a 19-gram difference per bird when comparing Test Vaccine 2 with the non-treated controls this difference amounts to an increase in total weight of 9.5 kg for the Test Vaccine 2 group over the non-treated control group. There was no difference in feed intake, but the Test Vaccine 2 group had improved feed efficiency as evidenced by the improved adjusted FCR.

Lesion scores on Day 34 (Johnson and Reid, 1970) were assessed as a measure of coccidial damage (E. acervulina, E. maxima, E. tenella and total average) to the gastrointestinal tract (Table 4 and FIG. 4A). Chickens vaccinated with Test Vaccine 2 had significantly lower lesion scores for all three Eimeria species and in total average lesion scores when compared to the non-treated controls. Average lesion scores were reduced by 42% in the Test Vaccine 2 group as compared to the non-treated controls; percent reduction in lesion scores for the individual Eimeria species between Test Vaccine 2 and non-treated control groups were as follows: EA 36%, EM 43% and ET 60%.

Moreover, on Days 28, 35 and 42 fresh fecal matter was collected from each experimental pen individually to determine coccidial shedding. Data generated from these analyses show total oocyst counts/gram of fecal matter the group treated with Test Vaccine 2 had a statistically significant initial 42% reduction (directly correlated to lesion scores reported above) in OPG counts at day 28 (Table 5 and FIG. 4B) and a subsequent statistically significant 83% reduction in OPG at both days 35 (Table 5 and FIG. 4C) and 42 (Table 5 and FIG. 4D) when compared to the non-treated control group. These data indicate that the protozoa is not replicating and is simply transient. This statement is further backed up by individual Eimeria oocyst counts at days 35 and 42 (Table 5 and FIGS. 4B and 4C) in which Eimeria maxima oocyst counts went to 0 at day 35 and remained there until the conclusion of the experiment in the Test Vaccine 2 group and Eimeria acervulina and Eimeria tenella oocyst counts are both approaching zero by the termination of the experiment in the Test Vaccine 2 group.

Clinical Trial 2 (Example 2)

The second trial was executed essentially the same as the first trial, with the exception that only Test Vaccine 2 was included. Data show that at day 21 (Table 6) Test Vaccine 2 had a slight numerical reduction in weight gain when compared to the non-treated group presumably due to intensity of immune response generated by vaccine administration at days 2 and 16; however, statistically average weight gain, feed intake and adjusted FCR were no different than the non-treated control (Table 6). Day 35 (Table 6) data show that there is a statistical difference between the Test Vaccine 2 group and the non-treated control group for adjusted FCR and DWG presumably due to the increased intensity of the challenge compared to Clinical Trial 1, Day 42 (Table 4), again statistical differences were observed in DWG and adjusted FCR when comparing the Test Vaccine 2 group with the non-treated controls with the Test Vaccine 2 vaccinated birds weighing an average of 155 g each more than the non-treated control birds.

Lesion scores on Day 34 (Johnson and Reid, 1970) were assessed as a measure of coccidial damage (E. acervulina, E. maxima, E. tenella and total average) to the gastrointestinal tract (Table 7 and FIG. 5A). Chickens vaccinated with Test Vaccine 2 had significantly lower lesion scores for all three Eimeria species and in total average lesion scores when compared to the non-treated controls. Average lesion scores were reduced by 45% in the Test Vaccine 2 group as compared to the non-treated controls; percent reduction in lesion scores for the individual Eimeria species between the Test Vaccine group and non-treated control groups were as follows: EA 39%, EM 39% and ET 66%.

Again, on Day 28, fresh fecal matter was collected from each experimental pen individually to determine coccidial shedding (Table 8 and FIG. 5B). Data generated from these analyses show total oocyst counts/gram of fecal matter for Test Vaccine 2 treated group had a statistically significant 65% reduction compared to the non-treated controls. Statistically significant reductions were also seen in each individual strain: EA 75%, EM 85% and ET 40% when comparing the Test Vaccine 2 treated animals against the non-treated control group.

Clinical Trial 3 (Example 3)

Data show that at day 21 (Table 9) the Test Vaccine 2 group had a slight numerical increase in weight gain when compared to the commercial vaccine group and the non-treated group; however, statistically average weight gain, feed intake and adjusted FCR were no different than the commercial vaccine group nor the non-treated control (Table 9). Day 35 (Table 9) data show that there is numerical difference but not a statistical difference between the Test Vaccine 2 group, the commercial vaccine group and the non-treated control group for BWG. The Test Vaccine 2 group and the commercial vaccine group are statistically different from the non-treated control group in both adjusted FCR and Feed Intake. Day 42 (Table 9), statistical differences were observed in DWG and adjusted FCR when comparing the Test Vaccine 2 group and the commercial vaccine group with the non-treated controls; with Test Vaccine 2 vaccinated birds weighing an average of 87 g more than the non-treated control birds and improving feed conversion by 84 points and a numerically improved feed conversion rate over the commercial vaccine (Table 9).

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied in other forms without departing from the spirit and the essential attributes thereof, and, accordingly, reference should be made to the appended claims, rather than to the foregoing specification, as indicating the scope of the invention. The invention illustratively disclosed herein suitably may be practiced in the absence of any element which is not specifically disclosed herein.

The invention claimed is:

1. A vaccine vector comprising:
a polynucleotide encoding the antigenic polypeptide selected from the group consisting of SEQ ID NO: 1, SEQ ID NO: 7, SEQ ID NO: 8, SEQ ID NO: 9, or any combination thereof.

2. The vaccine vector of claim 1 wherein the vaccine vector is a bacterium.

3. The vaccine vector of claim 2, wherein the bacterial vaccine vector is a *Bacillus* spp.

4. The vaccine vector of claim 1 further comprising one or more immunostimulatory polypeptides.

5. The vaccine vector of claim 1 wherein the antigenic polypeptide is present on the surface of the vaccine vector.

6. A pharmaceutical composition comprising the vaccine vector of claim 1 and a pharmaceutically acceptable carrier.

7. A vaccine vector comprising:

a polynucleotide encoding the antigenic polypeptide selected from the group consisting of SEQ ID NO: 1, SEQ ID NO: 8, SEQ ID NO: 9, or any combination thereof.

8. The vaccine vector of claim 7 wherein the vaccine vector is a bacterium.

9. The vaccine vector of claim 8, wherein the bacterial vaccine vector is a *Bacillus* spp.

10. The vaccine vector of claim 7 further comprising one or more immunostimulatory polypeptides.

11. The vaccine vector of claim 7 wherein the antigenic polypeptide is present on the surface of the vaccine vector.

12. A pharmaceutical composition comprising the vaccine vector of claim 7 and a pharmaceutically acceptable carrier.

* * * * *

```
                         SEQUENCE LISTING

<160> NUMBER OF SEQ ID NOS: 9

<210> SEQ ID NO 1
    <211> LENGTH: 103
    <212> TYPE: PRT
    <213> ORGANISM: Artificial sequence
    <220> FEATURE:
    <223> OTHER INFORMATION: Sequence is synthesized

<400> SEQUENCE: 1

Ser Thr Pro Pro Pro Ser Pro Pro Ala Gln Pro Thr Pro Gln Pro Gln
    1               5                   10                  15

Pro His Pro Pro Pro Gln Pro Glu Thr Pro Pro Ser Ala Pro Ser Pro
                    20                  25                  30

Pro Pro Pro Thr Pro Pro Ser Ala Pro Ser Pro Ser Pro Arg Thr Pro
                35                  40                  45

Pro Ser Ala Pro Ser Pro Ser Pro Arg Ala Pro Ser Pro Pro Pro Pro
            50                  55                  60

Thr Pro Pro Cys Ala Pro Ser Pro Ser Pro Pro Thr Pro Pro Pro Gly
    65                  70                  75                  80

Ser Pro His Lys Pro Ser Pro Pro Pro Ser Pro Pro Pro Thr Glu Ser
                    85                  90                  95

Ala Pro Gly Ala Pro Pro Ser
                    100

<210> SEQ ID NO 2
    <211> LENGTH: 25
    <212> TYPE: PRT
    <213> ORGANISM: Artificial sequence
    <220> FEATURE:
    <223> OTHER INFORMATION: Sequence is synthesized

<400> SEQUENCE: 2

Ser Thr Pro Pro Pro Ser Pro Pro Ala Gln Pro Thr Pro Gln Pro Gln
    1               5                   10                  15

Pro His Pro Pro Pro Gln Pro Glu Thr
                    20                  25

<210> SEQ ID NO 3
    <211> LENGTH: 25
    <212> TYPE: PRT
    <213> ORGANISM: Artificial sequence
    <220> FEATURE:
    <223> OTHER INFORMATION: Sequence is synthesized

<400> SEQUENCE: 3

Pro Pro Gln Pro Glu Thr Pro Pro Ser Ala Pro Ser Pro Pro Pro Pro
    1               5                   10                  15

Thr Pro Pro Ser Ala Pro Ser Pro Ser
                    20                  25
```

<210> SEQ ID NO 4
<211> LENGTH: 25
<212> TYPE: PRT
<213> ORGANISM: Artificial sequence
<220> FEATURE:
<223> OTHER INFORMATION: Sequence is synthesized

<400> SEQUENCE: 4

Pro Pro Pro Thr Pro Pro Ser Ala Pro Ser Pro Ser Pro Arg Thr Pro
1               5                   10                  15

Pro Ser Ala Pro Ser Pro Ser Pro Arg
            20                  25

<210> SEQ ID NO 5
<211> LENGTH: 25
<212> TYPE: PRT
<213> ORGANISM: Artificial sequence
<220> FEATURE:
<223> OTHER INFORMATION: Sequence is synthesized

<400> SEQUENCE: 5

Ala Pro Ser Pro Pro Pro Pro Thr Pro Pro Cys Ala Pro Ser Pro Ser
1               5                   10                  15

Pro Pro Thr Pro Pro Pro Gly Ser Pro
            20                  25

<210> SEQ ID NO 6
<211> LENGTH: 25
<212> TYPE: PRT
<213> ORGANISM: Artificial sequence
<220> FEATURE:
<223> OTHER INFORMATION: Sequence is synthesized

<400> SEQUENCE: 6

Pro Pro Pro Pro Thr Pro Pro Cys Ala Pro Ser Pro Ser Pro Pro Thr
1               5                   10                  15

Pro Pro Pro Gly Ser Pro His Lys Pro
            20                  25

<210> SEQ ID NO 7
<211> LENGTH: 18
<212> TYPE: PRT
<213> ORGANISM: Artificial sequence
<220> FEATURE:
<223> OTHER INFORMATION: Sequence is synthesized

<400> SEQUENCE: 7

Ser Pro Pro Pro Ser Pro Pro Pro Thr Glu Ser Ala Pro Gly Ala Pro
1               5                   10                  15

Pro Ser

<210> SEQ ID NO 8
<211> LENGTH: 640
<212> TYPE: PRT
<213> ORGANISM: Artificial sequence
<220> FEATURE:
<223> OTHER INFORMATION: Sequence is synthesized

<400> SEQUENCE: 8

Gly Gly Gly Met Ser Gly Lys Gly Pro Ala Ile Gly Ile Asp Leu Gly
1               5                   10                  15

Thr Thr Tyr Ser Cys Val Gly Val Phe Gln His Gly Lys Val Glu Ile
            20                  25                  30

-continued

```
Ile Ala Asn Asp Gln Gly Asn Arg Thr Thr Pro Ser Tyr Val Ala Phe
         35                  40                  45

Thr Asp Thr Glu Arg Leu Ile Gly Asp Ala Ala Lys Asn Gln Val Ala
 50                  55                  60

Met Asn Pro Thr Asn Thr Ile Phe Asp Ala Lys Arg Leu Ile Gly Arg
 65                  70                  75                  80

Lys Tyr Asp Asp Pro Thr Val Gln Ser Asp Met Lys His Trp Pro Phe
                 85                  90                  95

Arg Val Val Asn Glu Gly Gly Lys Pro Lys Val Gln Val Glu Tyr Lys
            100                 105                 110

Gly Glu Met Lys Thr Phe Phe Pro Glu Glu Ile Ser Ser Met Val Leu
        115                 120                 125

Thr Lys Met Lys Glu Ile Ala Glu Ala Tyr Leu Gly Lys Lys Val Glu
    130                 135                 140

Thr Ala Val Ile Thr Val Pro Ala Tyr Phe Asn Asp Ser Gln Arg Gln
145                 150                 155                 160

Ala Thr Lys Asp Ala Gly Thr Ile Thr Gly Leu Asn Val Met Arg Ile
                165                 170                 175

Ile Asn Glu Pro Thr Ala Ala Ile Ala Tyr Gly Leu Asp Lys Lys
            180                 185                 190

Gly Thr Arg Ala Gly Glu Lys Asn Val Leu Ile Phe Asp Leu Gly Gly
        195                 200                 205

Gly Thr Phe Asp Val Ser Ile Leu Thr Ile Glu Asp Gly Ile Phe Glu
    210                 215                 220

Val Lys Ser Thr Ala Gly Asp Thr His Leu Gly Gly Glu Asp Phe Asp
225                 230                 235                 240

Asn Arg Met Val Asn Arg Phe Val Glu Glu Phe Lys Gly Lys His Lys
                245                 250                 255

Arg Asp Asn Ala Gly Asn Lys Arg Ala Val Arg Arg Leu Arg Thr Ala
            260                 265                 270

Cys Glu Arg Ala Arg Arg Thr Leu Ser Ser Ser Thr Gln Ala Ser Ile
        275                 280                 285

Glu Ile Asp Ser Leu Phe Glu Gly Ile Asp Phe Tyr Thr Ser Ile Thr
    290                 295                 300

Arg Ala Arg Phe Glu Glu Leu Asn Ala Asp Leu Phe Arg Gly Thr Leu
305                 310                 315                 320

Glu Pro Val Glu Lys Ala Leu Arg Asp Ala Lys Leu Asp Lys Gly Gln
                325                 330                 335

Ile Gln Glu Ile Val Leu Val Gly Gly Ser Thr Arg Ile Pro Lys Ile
            340                 345                 350

Gln Lys Leu Leu Gln Asp Phe Phe Asn Gly Lys Glu Leu Asn Lys Ser
        355                 360                 365

Ile Asn Pro Asp Glu Ala Val Ala Tyr Gly Ala Ala Val Gln Ala Ala
    370                 375                 380

Ile Leu Met Gly Asp Lys Ser Glu Asn Val Gln Asp Leu Leu Leu Leu
385                 390                 395                 400

Asp Val Thr Pro Leu Ser Leu Gly Ile Glu Thr Ala Gly Gly Val Met
                405                 410                 415

Thr Ala Leu Ile Lys Arg Asn Thr Thr Ile Pro Thr Lys Gln Thr Gln
            420                 425                 430

Thr Phe Thr Thr Tyr Ser Asp Asn Gln Ser Ser Val Leu Val Gln Val
        435                 440                 445

Tyr Glu Gly Glu Arg Ala Met Thr Lys Asp Asn Asn Leu Leu Gly Lys
```

```
                450                 455                 460
Phe Asp Leu Thr Gly Ile Pro Pro Ala Pro Arg Gly Val Pro Gln Ile
465                 470                 475                 480

Glu Val Thr Phe Asp Ile Asp Ala Asn Gly Ile Leu Asn Val Ser Ala
                485                 490                 495

Val Asp Lys Ser Thr Gly Lys Glu Asn Lys Ile Thr Ile Thr Asn Asp
            500                 505                 510

Lys Gly Arg Leu Ser Lys Asp Asp Ile Asp Arg Met Val Gln Glu Ala
            515                 520                 525

Glu Lys Tyr Lys Ala Glu Asp Glu Ala Asn Arg Asp Arg Val Gly Ala
        530                 535                 540

Lys Asn Ser Leu Glu Ser Tyr Thr Tyr Asn Met Lys Gln Thr Val Glu
545                 550                 555                 560

Asp Glu Lys Leu Lys Gly Lys Ile Ser Asp Gln Asp Lys Gln Lys Val
                565                 570                 575

Leu Asp Lys Cys Gln Glu Val Ile Ser Ser Leu Asp Arg Asn Gln Met
            580                 585                 590

Ala Glu Lys Glu Glu Tyr Glu His Lys Gln Lys Glu Leu Glu Lys Leu
        595                 600                 605

Cys Asn Pro Ile Val Thr Lys Leu Tyr Gln Gly Ala Gly Gly Ala Gly
610                 615                 620

Ala Gly Gly Ser Gly Gly Pro Thr Ile Glu Glu Val Asp Gly Gly
625                 630                 635                 640

<210> SEQ ID NO 9
<211> LENGTH: 795
<212> TYPE: PRT
<213> ORGANISM: Artificial sequence
<220> FEATURE:
<223> OTHER INFORMATION: Sequence is synthesized

<400> SEQUENCE: 9

Ser Thr Pro Pro Ser Pro Pro Ala Gln Pro Thr Pro Gln Pro Gln
1               5                   10                  15

Pro His Pro Pro Gln Pro Glu Thr Ser Ser Pro Pro Gln Pro
            20                  25                  30

Glu Thr Pro Pro Ser Ala Pro Ser Pro Pro Pro Thr Pro Pro Ser
        35                  40                  45

Ala Pro Ser Pro Ser Ser Ser Pro Pro Thr Pro Pro Ser Ala
    50                  55                  60

Pro Ser Pro Ser Pro Arg Thr Pro Pro Ser Ala Pro Ser Pro Ser Pro
65                  70                  75                  80

Arg Gly Gly Gly Met Ser Gly Lys Gly Pro Ala Ile Gly Ile Asp Leu
                85                  90                  95

Gly Thr Thr Tyr Ser Cys Val Gly Val Phe Gln His Gly Lys Val Glu
            100                 105                 110

Ile Ile Ala Asn Asp Gln Gly Asn Arg Thr Thr Pro Ser Tyr Val Ala
        115                 120                 125

Phe Thr Asp Thr Glu Arg Leu Ile Gly Asp Ala Ala Lys Asn Gln Val
    130                 135                 140

Ala Met Asn Pro Thr Asn Thr Ile Phe Asp Ala Lys Arg Leu Ile Gly
145                 150                 155                 160

Arg Lys Tyr Asp Asp Pro Thr Val Gln Ser Asp Met Lys His Trp Pro
                165                 170                 175

Phe Arg Val Val Asn Glu Gly Gly Lys Pro Lys Val Gln Val Glu Tyr
```

```
                180                 185                 190
Lys Gly Glu Met Lys Thr Phe Phe Pro Glu Glu Ile Ser Ser Met Val
            195                 200                 205
Leu Thr Lys Met Lys Glu Ile Ala Glu Ala Tyr Leu Gly Lys Lys Val
            210                 215                 220
Glu Thr Ala Val Ile Thr Val Pro Ala Tyr Phe Asn Asp Ser Gln Arg
225                 230                 235                 240
Gln Ala Thr Lys Asp Ala Gly Thr Ile Thr Gly Leu Asn Val Met Arg
                245                 250                 255
Ile Ile Asn Glu Pro Thr Ala Ala Ile Ala Tyr Gly Leu Asp Lys
                260                 265                 270
Lys Gly Thr Arg Ala Gly Glu Lys Asn Val Leu Ile Phe Asp Leu Gly
            275                 280                 285
Gly Gly Thr Phe Asp Val Ser Ile Leu Thr Ile Glu Asp Gly Ile Phe
            290                 295                 300
Glu Val Lys Ser Thr Ala Gly Asp Thr His Leu Gly Gly Glu Asp Phe
305                 310                 315                 320
Asp Asn Arg Met Val Asn Arg Phe Val Glu Glu Phe Lys Gly Lys His
                325                 330                 335
Lys Arg Asp Asn Ala Gly Asn Lys Arg Ala Val Arg Arg Leu Arg Thr
                340                 345                 350
Ala Cys Glu Arg Ala Arg Arg Thr Leu Ser Ser Ser Thr Gln Ala Ser
            355                 360                 365
Ile Glu Ile Asp Ser Leu Phe Glu Gly Ile Asp Phe Tyr Thr Ser Ile
            370                 375                 380
Thr Arg Ala Arg Phe Glu Glu Leu Asn Ala Asp Leu Phe Arg Gly Thr
385                 390                 395                 400
Leu Glu Pro Val Glu Lys Ala Leu Arg Asp Ala Lys Leu Asp Lys Gly
                405                 410                 415
Gln Ile Gln Glu Ile Val Leu Val Gly Gly Ser Thr Arg Ile Pro Lys
                420                 425                 430
Ile Gln Lys Leu Leu Gln Asp Phe Phe Asn Gly Lys Glu Leu Asn Lys
            435                 440                 445
Ser Ile Asn Pro Asp Glu Ala Val Ala Tyr Gly Ala Ala Val Gln Ala
            450                 455                 460
Ala Ile Leu Met Gly Asp Lys Ser Glu Asn Val Gln Asp Leu Leu Leu
465                 470                 475                 480
Leu Asp Val Thr Pro Leu Ser Leu Gly Ile Glu Thr Ala Gly Gly Val
                485                 490                 495
Met Thr Ala Leu Ile Lys Arg Asn Thr Thr Ile Pro Thr Lys Gln Thr
                500                 505                 510
Gln Thr Phe Thr Thr Tyr Ser Asp Asn Gln Ser Ser Val Leu Val Gln
            515                 520                 525
Val Tyr Glu Gly Glu Arg Ala Met Thr Lys Asp Asn Leu Leu Gly
            530                 535                 540
Lys Phe Asp Leu Thr Gly Ile Pro Pro Ala Pro Arg Gly Val Pro Gln
545                 550                 555                 560
Ile Glu Val Thr Phe Asp Ile Asp Ala Asn Gly Ile Leu Asn Val Ser
                565                 570                 575
Ala Val Asp Lys Ser Thr Gly Lys Glu Asn Lys Ile Thr Ile Thr Asn
                580                 585                 590
Asp Lys Gly Arg Leu Ser Lys Asp Asp Ile Asp Arg Met Val Gln Glu
            595                 600                 605
```

-continued

```
Ala Glu Lys Tyr Lys Ala Glu Asp Glu Ala Asn Arg Asp Arg Val Gly
    610                 615                 620

Ala Lys Asn Ser Leu Glu Ser Tyr Thr Tyr Asn Met Lys Gln Thr Val
625                 630                 635                 640

Glu Asp Glu Lys Leu Lys Gly Lys Ile Ser Asp Gln Asp Lys Gln Lys
                645                 650                 655

Val Leu Asp Lys Cys Gln Glu Val Ile Ser Ser Leu Asp Arg Asn Gln
            660                 665                 670

Met Ala Glu Lys Glu Glu Tyr Glu His Lys Gln Lys Glu Leu Glu Lys
        675                 680                 685

Leu Cys Asn Pro Ile Val Thr Lys Leu Tyr Gln Gly Ala Gly Gly Ala
    690                 695                 700

Gly Ala Gly Gly Ser Gly Gly Pro Thr Ile Glu Glu Val Asp Gly Gly
705                 710                 715                 720

Gly Ala Pro Ser Pro Pro Pro Pro Thr Pro Pro Cys Ala Pro Ser Pro
                725                 730                 735

Ser Pro Pro Thr Pro Pro Pro Gly Ser Pro Ser Ser Ser Pro Pro Pro
            740                 745                 750

Pro Thr Pro Pro Cys Ala Pro Ser Pro Ser Pro Pro Thr Pro Pro Pro
        755                 760                 765

Gly Ser Pro His Lys Pro Ser Ser Ser Ser Pro Pro Pro Ser Pro Pro
    770                 775                 780

Pro Thr Glu Ser Ala Pro Gly Ala Pro Pro Ser
785                 790                 795
```